United States Patent [19]

Veech

[11] Patent Number: 4,663,289
[45] Date of Patent: May 5, 1987

[54] ELECTROLYTE SOLUTIONS AND IN VITRO USE THEREOF

[76] Inventor: Richard L. Veech, 712 Brent Rd., Rockville, Md. 20850

[21] Appl. No.: 747,792

[22] Filed: Jun. 24, 1985

Related U.S. Application Data

[63] Continuation of Ser. No. 623,510, Jun. 22, 1984, abandoned.

[51] Int. Cl.$^4$ ............................ C12N 5/00; A01N 1/02
[52] U.S. Cl. ...................................... 435/240; 435/1; 435/2; 435/241; 435/260; 424/127; 424/128; 424/153; 424/154; 514/23; 514/2
[58] Field of Search ............ 435/240, 241, 1, 2, 435/243, 244, 247, 248–250, 260; 424/127, 128, 149, 154, 177, 180, 153; 47/59, 62

[56] References Cited

U.S. PATENT DOCUMENTS

| | | | |
|---|---|---|---|
| Re. 30,985 | 6/1982 | Cartaya | 435/241 |
| 3,122,476 | 2/1964 | Gaeta . | |
| 3,128,228 | 4/1964 | Michl | 435/240 |
| 3,356,570 | 12/1967 | Butcher | 424/153 |
| 3,821,368 | 6/1974 | Reynolds | 424/128 |
| 3,978,212 | 8/1976 | Barna | 424/154 |
| 3,993,751 | 11/1976 | Zinke | 424/128 |
| 4,018,649 | 4/1977 | Cone, Jr. | 435/241 |
| 4,061,537 | 12/1977 | Seiler | 435/1 |
| 4,186,253 | 1/1980 | Yokoyama | 435/240 |
| 4,282,326 | 8/1981 | Moldenhauer | 435/240 |
| 4,308,255 | 12/1981 | Raj | 424/153 |
| 4,404,192 | 9/1983 | Suzuki | 424/153 |
| 4,443,432 | 4/1984 | Garabedian | 424/127 |
| 4,443,546 | 4/1984 | Stemerman | 435/240 |
| 4,447,415 | 5/1984 | Rock | 435/1 |
| 4,473,647 | 9/1984 | Carpenter | 435/240 |
| 4,476,221 | 10/1984 | Kane | 435/2 |
| 4,489,535 | 12/1984 | Veltman | 424/153 |
| 4,508,819 | 4/1985 | Rose | 435/240 |

FOREIGN PATENT DOCUMENTS

| | | |
|---|---|---|
| WO86/239 | 1/1986 | PCT Int'l Appl. . |
| WO86/227 | 1/1986 | PCT Int'l Appl. . |
| WO86/228 | 1/1986 | PCT Int'l Appl. . |
| WO86/335 | 1/1986 | PCT Int'l Appl. . |
| 0905281 | 2/1982 | U.S.S.R. ............................ 435/240 |

OTHER PUBLICATIONS

Latta, T., (1832), Malignant Cholera. Documents . . . Relative to the Treatment of Cholera by Copious Injection of Aqueous & Saline Fluids into the Veins, *Lancet ii*; 272–277.

Ringer, S., (1883), A Further Contribution Regarding the Influence of the Different Constituents of the Blood on the Contraction of the Heart, *J. Physiol*, 4: 29–42.

Hartman, A. F., (1934), Theory & Practice of Parenteral Fluid Administration, *JAMA*, 103: 1349–1354.

Locke, F. S., (1900), Die Wirkung der Metalle des Blutplasma & Verschiedener Zucker auf das Isolirte Saugerthierherz, *Zentrablatt fuer Physiologie*, 14: 670–673.

Tyrode, M. N., (1910), The Mode of Action of Some Purgative Salts, *Arch int. Pharmacedyn*, 20: 205–223.

Krebs, H. A., Henseleit, K., (1932), Untersuchugen Uber die Harnstoffbildung im Tierkorper., *Hoppe-Seyler's Z Physiol Chem*, 210: 33–66.

Dawson, A. M. C., Elliott, D., Elliot, W. H., Jone, K. M., (1969), Data for Biochemical Research, 2nd Ed., Clarendon Press, Oxford, p. 507, "Physiological Media".

Fox, Ch., Winfield, J. M., Slobody, L. B., Swindler, C. M., Lattimer, J. K. (1952), Electrolyte Solution Approximating Plasma Concentrations with Increased Potassium for Routine Fluid & Electrolyte Replacement, *JAMA*, 148, 827–833.

Mion, C. M., Hegstrom, R. M., Boen, St, Scribner, B. H., (1964), Substitution of Sodium Acetate for Sodium Bicarbonate in the Bath for Hemodialysis, *Trans Amer Soc Artif Int. Organs*, 10: 110–113.

Parsons, F. M., Stewart, W. K., (1983), The Composition of Dialysis Fluid. In: Replacement of Renal Function by Dialysis, 2nd ed. (Drukker, W., Parsons, F. M., Maher, J. F., eds), Martinus Nijhoff, Higham, pp. 148–170.

*Facts and Comparisons*, Oct. 1981–Aug. 1983, J. B. Lippincott: St. Louis, 35d–53.

*Documenta Geigy Scientific Tables* (1962 Essellier, A. F., Jeanneret, P., Aqueous Solutions–Parenteral Infusion Therapy. pp. 331–334, Geigy Pharmaceutical Co Ltd., Manchester.

Merck Manual, 12th Ed. (1972), Electrolytic, Caloric and Water Balance Agents. pp. 1866–1867.

Veech, R. L., Eggleston, L. V., Krebs, H. A., (1969), The Redox State of Free Nicotin Amide–Adenine Dinucleotide Phosphate in the Cytoplasm of Rat Liver, *Biochem J*, 115, 609–619.

Veech, R. L., Lawson, J. W. R., Cornell, N. W., Krebs, H. S., (1979), Cytosolic Phosphorylation Potential, *J Biol Chem*, 254: 6538–6547.

(List continued on next page.)

*Primary Examiner*—Charles F. Warren
*Assistant Examiner*—M. Moskowitz
*Attorney, Agent, or Firm*—Hill, Van Santen, Steadman & Simpson

[57] ABSTRACT

Processes and compositions are provided for in vitro use in tissue culture media (preferred), perfusion media, and incubation media. Thus, balanced salt solutions are provided wherein the milliequivalent ratio of sodium cations to chloride anions is normalized and wherein optionally at least one near-equilibrium couple is incorporated (bicarbonate$^-$/carbon dioxide, L-lactate$^-$/pyruvate$^-$, and d-betahydroxybutyrate/acetoacetate$^-$. Regulation of intracellular and extracellular pH, and normalization of intracellular redox state and phosphorylation state is achievable.

14 Claims, No Drawings

OTHER PUBLICATIONS

Veech, R. L., Cook, G. A., King, M. T., (1980), Relationship of Free Cytoplasmic Pyrophosphate to Liver Glucose Content & Total Pyrophosphate to Cyoplasmic Phosphorylation Potential, FEBS Lett, 117: K65–K72.

Sistare, F. D., Haynes, R. C., Jr., (1985), The Interaction Between the Cytosolic Pyridine Mucleotide Redox Potential & Gluconeogenisis from Lactate/Pyruvate in Isolated Rat Hepatocytes. J Biol Chem, 260, 12748–12753.

Sistare, F. D., Haynes, R. C., Jr., (1985), Acute Stimulation by Gluconeogenisis from Lactanate/Pyruvate In Isolated Hepatocytes from Normal and Adrenolectonized Rats. J Biol Chem, 260: 1254–12760.

Veech, R. L., (1986), The Toxic Impact of Parenteral Fluid Therapy, J Clin Nutr (In Press).

Tauford, C. S., (1950), J Am Chem Soc, 72: 441–451, Preparation & Properties of Serum Plasma Proteins. XXIII. Hydrogen Ion Equilibria in Nature & Modified Human Serum Albumin.

ELECTROLYTE SOLUTIONS AND IN VITRO USE THEREOF

This application is a continuation-in-part application of U.S. Ser. No. 623,510 filed June 22, 1984, now abandoned.

BACKGROUND OF THE INVENTION

1. Field of the Invention

This invention lies in the field of in vitro techniques and compositions for replenishing fluid electrolytes and nutrients while regulating metabolic processes in living animal cells.

2. State of the Art

The vital functions of highly developed organisms are closely dependent on the internal aqueous medium and on the maintenance in it of extreme constancy of chemical and physical properties.

Typically in vitro fluids of this type are aqueous electrolyte solutions which are used to contact living cells in, for examples, (1) incubation of tissue slices, minces or homogenates, (2) perfusion of isolated organs as kidney's, liver, muscles, or heart, (3) incubations of isolated cell suspensions such as isolated adipocytes, hepatocytes, blood cells, myocytes etc., and (4) most particularly, electrolytes or "balanced salt mixtures" in which cells in culture are grown after the optional addition thereto of a host of various nutrients, such as vitamins, sugars, amino acids, hormones, and the like. As will be shown all of other famous solutions, e.g., Hank's (*Proc Soc Exp Biol Med* 71: 196, 1949), Delbecco's (*J Exp Med* 99: 167-182, 1954), Earle's (*J Nat'l Canc Inst* 4: 165-212, 1943), etc., used in the tissue culture art are very simple variations of only 2 basic electrolyte solutions—usually Krebs-Henseleit (Krebs H A, Henseleit K A. *Hoppe-Seyler's Z Physiol* 210:33-66, 1932) with variations for the excessive $Ca^{2+}$ used by Krebs, and Krebs-ringer-Phosphate (Krebs H A. *Hoppe-Seyler's Z Physiol Chem* 217: 193, 1933), where for convenience of the Experimenter buffering of the pH is achieved with excessive Pi (inorganic phosphate) rather than with $HCO_3^-/CO_2$.

In this disclosure we propose the first major basic advance in these fundamental (basic) electrolyte solutions for the in vitro art since Kreb's attempted to correct the abnormal Na:Cl ratio present in all such solutions in 1950 (Krebs H A. *Biochem Biophys Acta* 4: 249-269, 1950).

It has long been recognized that all animal intracellular and extracellular body fluids contain inorganic electrolytes, and that these electrolytes are involved in, and profoundly influence, various life processes. Attempts to make artifical electrolyte fluids which may bathe tissues or be administered to the human blood stream have been known since about 1880, and, although modern analytical tools and procedures have clarified compositional details of blood electrolytes, the use of varous aqueous electrolyte solutions for in vitro purposes in tissue culture, organ perfusion and related fields has long been extant.

Those inorganic electrolytes characteristically found in normal human blood serum at respective concentration levels above about 1 millimolar per liter of concentration are shown below in Table I. Also, for comparative purposes, in Table I are shown some representative compositions of various aqueous electrolyte solutions that have been previously prepared and used for in vitro purposes. In general, the philosophy behind the formaluation of aqueous electrolyte solutions for in vitro use has been that such should mimic or closely resembled the chemical composition of electrolytes in blood, (plasma) extracellular fluids and intracellular fluids. An electrolyte is a substance (usually a salt, acid or base) which in solution dissociates wholly or partly into electrically charged particles known as ions (the term is also sometimes used inthe art to denote the solution itself, whichhas a higher electrical conductivity than the pure solvent, e.g. water). The positively charged ions are termed cations while the negatively charged ions are termed anions. Strong and weak electrolytes are recognized. The dissociation of electrolytes is very markedly dependent on concentration; it increases with increasing dilution of the solution. The ions can be regarded as molecules in electrolyte solution. Because of dissociation considerations, the term "sigma" or the greek letter for sigma ("Σ") is sometimes employed herein as a prefix to designate the total presence of a specified material, such as an electrolyte, whether or not all of the material is in an ionic form complexed with a heavy metal, or regardless of charge on the material in a given solution. A pair of brackets [ ] indicates the free concentration of the substance indicated as opposed to that bound to tissue components, such as proteins.

TABLE I

Prior Art Simulated Plasma Electrolyte Solutions for Contacting Living Cells in Vitro.

| Units mmoles L fluid | Normal Plasma N.E.J.M. 283, 1285 1970 | (1) Normal Saline 0.9% NaCl U.S. | (2) Normal Saline 0.95% NaCl U.K. | (3) Ringer's Injection U.S. | (4) Mammalian Ringer's U.K. & Canada | (5) Lactated Ringer's U.S. | (6) Lactated Ringer's (Hartmann) | (7) Acetated Ringer's | (8) Locke's | (9) Tyrode's | (10) Krebs Henseleit | (11) Krebs Ringer Phosphate | (12) Krebs Serum Substitute | (13) Krebs Improved Ringer II $Ca^{2+}$ free | (14) Krebs Improved Ringer III Low $HCO_3^-$ Low Pi |
|---|---|---|---|---|---|---|---|---|---|---|---|---|---|---|---|
| Na | 136–145 | 154 | 162.5 | 147 | 156.4 | 130 | 129.8 | 130 | 157.57 | 150.1 | 143 | 150.76 | 140.31 | 147.41 | 140.86 |
| K | 3.5–5.0 | | | 4 | 5.4 | 4 | 5.4 | 4 | 3.57 | 5.9 | 5.9 | 5.92 | 5.92 | 5.92 | 5.92 |
| Ca | 2.1–2.6 | | | 2.5 | 1.15 | 1.5 | 0.9 | 1.5 | 2.16 | 1.8 | 2.5 | 2.54 | 2.54 | | 2.54 |
| free [$Ca^{2+}$] | [1.06] | | | | | | | | | | | | | | |
| Mg | 0.75–1.25 | | | | | | 1.0 | | | 0.45 | 1.2 | 1.18 | 1.18 | 1.18 | 1.18 |
| free [$Mg^{2+}$] | [0.53] | | | | | | | | | | | | | | |
| Σ mEq Cations | 142.7–153.2 | 154 | 162.5 | 156 | 164.1 | 137 | 139 | 137 | 165.46 | 160.5 | 156.3 | 164.12 | 153.7 | 155.69 | 154.22 |
| Cl | 100–106 | 154 | 162.5 | 156 | 161.7 | 109 | 111.8 | 109 | 163.92 | 147.48 | 127.8 | 131.51 | 104.62 | 103.06 | 122.36 |
| $HCO_3$ | 26–28 | | | | 2.4 | | | | | | 25 | | 24.9 | | 3.56 |
| Σ Pi | 1–1.45 | | | | | | | | 3.57 | 11.9 | 1.18 | 17.38 | 1.18 | 15.03 | 3.49 |
| $SO_4$ | 0.32–0.94 | | | | | | | | | 1.22 | 1.18 | 1.18 | 1.18 | 1.18 | 1.18 |
| L-lactate | 0.6–1.8 | | | | | 28(d,l) | 27.2(d,l) | | | | | | | | |
| Lact/pyr | | | | | | | | | | | | | | | |
| D-β-OHbutyrate | | | | | | | | | | | | | | | |
| acetoacetate | | | | | | | | | | | | | | | |
| β-HB/acac | | | | | | | | | | | | | | | |
| acetate | | | | | | | | 28 | | | | | | 4.92 | 4.92 |
| Other | | | | | | | | | | | | fumarate$^{2-}$ glutamate$^-$ | | | |
| Σ mEq anions | 128.7–139.4 | 154 | 162.5 | 156 | 164.1 | 137 | 139 | 137 | 167.49 | 161.6 | 157.3 | 163.97 | 152.49 | 156.64 | 155.17 |
| Na/Cl | 1.28–1.45 | 1.00 | 1.00 | 0.94 | 0.97 | 1.23 | 1.16 | 1.19 | 0.96 | 1.02 | 1.12 | | 1.34 | 1.43 | 1.15 |
| Glucose or others | 3.9–5.6 | | | | | | | | 5.6–13.9 | 5.6 | | 1.15 | 11.5 | 11.5 | 11.5 |
| $CO_2$ | 0.99–1.39 | | | | | | | | | | 1.24 | | 1.24 | | |
| pH | 7.35–7.45 | ≈5.5–6.5 | ≈5.5–6.5 | ≈5.5–6.5 | ≈7.0 | | | | | 7.1 | 7.4 | 7.4 | 7.4 | ≈7.6 | ≈7.6 |
| Σ mOsm | 285–295 | 308 | 325 | 309 | 324 | 272.5 | 276 | 272.5 | 336 | 318.8 | 308 | 311.7 | 309.8 | 304.1 | 307.8 |
| Use: | | | | | | | | | | | | | | | |

(1) Usual "physiological saline" in the U.S. is a 0.9% or 154 mM. (Gilman AG, Goodman LS, Gilman A. The Pharmacological Basis of Theraputics (1980) pp 848–884, McMillan, London.
(2) "Physiological Saline" in the U.K. is 0.95% NaCl. (Diem K. ed. Documenta Geigy (1962) pp 333–334, Geigy, Manchester.
(3) All "Ringer's solutions" are derived from Ringer S. Physiol 4, 29, & 222, 1893 and 7, 1886. This commercial U.S. version is from Facts and Comparisons, Oct 1981. p. 50. Lippincott, St. Louis.
(4) From Best and Taylor, Physiological Basis of Medical Practice, 6th edition, Baltimore, 1950.
(5) From Facts and Comparisons p. 50, Oct '81, Lippincott, St. Louis.
(6) Hartmann AF. J Am Med Assoc 103: 1349–1354, 1934.
(7) Fox CL et al. J Am Med Assoc 148: 825–833, 1952.
(8) Locke FS. Zbl Physiol 8,166, 1894; 14, 670, 1900; 15, 490, 1901.
(9) Tyrode MJ. Arch int Pharmacodyn 20, 205, 1910.
(10) Krebs HA, Henseleit KA. Hoppe-Seyle's Z Physiol Chem 210, 33–66, 1932.
(11) Krebs HA. Hoppe-Seyle's Z Physiol Chem 217, 193, 1933.
(12)–(14) Krebs HA. Biochem Biophys Acta 4, 249–269, 1950.

TABLE II

"Prior Art Perfusion Fluids"

| Units mmoles L fluid | Normal Plasma N.E.J.M. 283, 1285 1970 | (15) Krebs Liver Perfusion with Bovine serum Albumin and Red Cells | (16) Schimassek Liver Perfusion | (17) Krebs Kidney Perfusion | (18) Hepatocyte Incubation | (19) Bahlman Kidney Perfusion | (20) Fulgraff Kidney Perfusion |
|---|---|---|---|---|---|---|---|
| Na | 136–145 | 153 | 151.54 | 148 | 153 | 147 | 143 |
| K | 3.5–5.0 | 5.9 | 5.9 | 5.9 | 5.9 | 4.9 | 4.74 |
| Ca | 2.1–2.6 | 2.5 | 1.8 | 2.5 | 2.5 | 2.56 | 1.25 |
| free [$Ca^{2+}$] | [1.06] | | | | | | |
| Mg | 0.75–1.25 | 1.2 | 0.49 | 1.2 | 1.2 | 1.2 | 0.59 |
| free [$Mg^{2+}$] | [0.53] | | | | | | |
| Σ mEq Cations | 142.7–153.2 | 166.3 | 162.02 | 161.3 | 166.3 | 159.4 | 151.15 |
| Cl | 100–106 | 127.8 | 147.48 | 127.8 | 127.8 | 127 | 113.04 |
| $HCO_3$ | 26–28 | 25 | 11.9 | 25 | 25 | 24.5 | 25 |
| Σ Pi | 1–1.45 | 1.18 | 1.22 | 1.18 | 1.18 | 1.18 | 1.18 |
| $SO_4$ | 0.32–0.94 | 1.18 | — | 1.2 | 1.2 | 1.18 | 1.18 |
| L-lactate | 0.6–1.8 | (10Na–1Lac) | 1.33 | 5Na—1Lac | 9.09 | 2.75(d,l) | 3.5(?d,l) |
| pyruvate | | | 0.09 | | 0.91 | 0.25 | 0.25 |
| Lact/pyr | | | 14.8 | | 10 | 10 | 7 or 14 |
| D-β-OHbutyrate | | | | | | | |
| acetoacetate | | | | | | | |
| β-HB/acac | | | | | | | |
| acetate | | | | | | | 5.0 |
| Other | | | | | | | |
| Σ mEq anions | 128.7–139.4 | 167.0 | 162.81 | 162.3 | 167.0 | 159.1 | 151.31 |
| Na/Cl | 1.28–1.45 | 1.12 (1.20) | 1.03 | 1.16 | 1.20 | 1.20 | 1.26 |
| Glucose | 3.9–5.6 | | 5.45 | | | 6.2 | — |
| or others | | | | | | 6.7 urea | 6.7 urea |
| $CO_2$ | 0.99–1.39 | 1.25 | 1.24 | 1.24 | 1.24 | 1.24 | 1.24 |
| pH | 7.35–7.45 | 7.4 | 7.1 | 7.4 | 7.4 | 7.4 | 7.4 |
| Σ mOsm | 285–295 | 328 | 321 | 318 | 328 | 327 | 307.9 |
| Albumin (g %) | 3.5–5 | 3.9 | 2.5 | 5 | 2.5 | 5.5 | 0.05 |

*Artificial perfusion fluid generally add 1.5 to 8 g % albumin, dialyzed against a medium listed in Table I; that is Krebs-Henseleit (10), Krebs-Ringer Phosphate (11), Tyrode's (9), Locke's (8), or Krebs-Henseleit with a lowered $Ca^{2+}$ to the 1 mM range, particularly in heart perfusion. They may or may not contain red cells. Krebs-Henseleit is known to contain about twice the amount of ionized $Ca^{2+}$ as serum.

(15) Hems R, Ross BD, Berry MN, Krebs HA. Biochem J 101, 284, 1966; Krebs Henseleit (10) with 3.9 g % bovine albumin.
(16) Schmassek H. Biochem Z 336, 460, 1963. Essentially Tyrode's (9) with added lactate and pyruvate.
(17) Nishiitsutsuji-Uwo JM, Ross BD, Krebs HA. Biochem J 103, 852-862, 1967; Krebs-Henseleit (10) with 5 g % albumin, dry.
(18) Crow KE, Cornell NW, Veech RL. Biochem J 172, 29-36, 1978, Krebs-Henseleit (10) with 2.5 g % dialysed albumin plus 1-lactate plus pyruvate.
(19) Bahlman J. et al. Am J Physiol 212, 77 1967; Krebs Henseleit (10) with lactate and pyruvate and 5.5 g % bovine albumin.
(20) Fulgraff et al. Arch int Pharmacodyn 172, 49, 1972; Krebs-Henseleit (10) with ½ Mg and Ca plus lactate and pyruvate, plus 5 mM acetate, plus 0.05 g % albumin plus 2 g % hemocel.

TABLE III

"Balanced Salt Mixtures" for Tissue Culture to Which are Added Complex Combined Nutrients of Carbohydrates, Vitamins, Amino Acids and Organic Acids as in Eagle's Basal Media (Eagle HJ. J Biol Chem 214, 839, 1955) which is Added to Earle's Salt Mixture.

| Units mmoles L fluid | Normal Plasma N.E.J.M 283, 1285 1970 | (10) Krebs Henseleit | (22) Earle's Balanced Salts | (23) William's | (24) Hank's Salts | (25) Ham's F-12 | (26) Delbecco's Phosphate Saline | (26a) Delbecco's Modified Eagle's | (11) Krebs Ringer Phosphate |
|---|---|---|---|---|---|---|---|---|---|
| Na | 136–145 | 143 | 142 | 144.3 | 142.8 | 146.9 | 152.2 | 154.5 | 150.76 |
| K | 3.5–5.0 | 5.9 | 5.4 | 5.4 | 5.8 | 3.0 | 4.17 | 5.4 | 5.92 |
| Ca | 2.1–2.6 | 2.5 | 1.8 | 1.81 | 1.3 | 0.3 | 0.9 | 1.8 | 2.54 |
| free [$Ca^{2+}$] | [1.06] | | | | | | | | |
| Mg | 0.75–1.25 | 1.2 | 0.8 | 0.81 | 0.8 | 0.6 | 0.49 | 0.8 | 1.18 |
| free [$Mg^{2+}$] | [0.53] | | | | | | | | |
| Σ mEq Cations | 142.7–153.2 | 156.3 | 152.6 | 154.9 | 152.8 | 151.7 | 159.15 | 165.1 | 164.12 |
| Cl | 100–106 | 127.8 | 126.2 | 126 | 146 | 133.6 | 140.5 | 118.5 | 131.51 |
| $HCO_3$ | 26–28 | 25 | 23.8 | 26 | 4.17 | 14 | — | 44 | — |
| Σ Pi | 1–1.45 | 1.18 | 1 | 1 | 0.8 | 1 | 9.83 | 1 | 17.38 |
| $SO_4$ | 0.32–0.94 | 1.18 | 0.8 | 0.8 | 0.8 | 0.6 | 0.48 | 0.8 | 1.18 |
| L-lactate | 0.6–1.8 | | | | | | | | |
| pyruvate | | | | 0.23 | | 0.9 | | 1.0 | |
| Lact/pyr | | | | 0 | | 0 | | 0 | |
| Other | | | | | | | | | |
| Σ mEq anions | 128.7–139.4 | 157.3 | 153.4 | 155.7 | 152.9 | 151.5 | 159.18 | 166.1 | 163.97 |
| Na/Cl | 1.28–1.45 | 1.12 | 1.12 | 1.15 | 0.975 | 1.10 | 1.08 | 1.30 | 1.15 |
| Glucose | 3.9–5.6 | — | 5.6 | 11.1 | 5.6 | 10 | — | 25 | — |
| or others | | | | | | | | | |
| $CO_2$ | 0.99–1.39 | 1.24 | 1.24 | 1.24 | — | 1.24 | — | 1.24 | — |
| pH | 7.35–7.45 | 7.4 | 7.4 | 7.4 | ≈7.6 | 7.1 | 7.4 | 7.65 | 7.4 |
| Σ mOsm | 285–295 | 308 | 311 | 321 | 308.2 | 312 | 308 | 354 | 311.7 |
| Use: | | | Tissue | Same as | Tissue | Tissue | Tissue | Tissue | |

TABLE III-continued
"Balanced Salt Mixtures" for Tissue Culture to Which are Added Complex Combined Nutrients of Carbohydrates, Vitamins, Amino Acids and Organic Acids as in Eagle's Basal Media (Eagle HJ. J Biol Chem 214, 839, 1955) which is Added to Earle's Salt Mixture.

| Units mmoles L fluid | Normal Plasma N.E.J.M 283, 1285 1970 | (10) Krebs Henseleit | (22) Earle's Balanced Salts | (23) William's | (24) Hank's Salts | (25) Ham's F-12 | (26) Delbecco's Phosphate Saline | (26a) Delbecco's Modified Eagle's | (11) Krebs Ringer Phosphate |
|---|---|---|---|---|---|---|---|---|---|
| | | | Culture Salts to which nutrients are added | 22 culture manipulation. | | Culture | | Culture | Culture |

(10) It can be seen that Earle's Balanced Salts and "Williams" are just Krebs-Henseleit with Mg and Ca decreased to more physiological levels. Both use $HCO_3/CO_2$. Both lack the proper NaCl ratio.
(22) Earle WR. et al. J Nat'l Canc Inst 4, 165-212, 1943. Used with 5% $CO_2$ and 20% $O_2$.
(23) Williams GM et al. Exp Cell Res 69, 106-112, 1971.
(24) Hanks JH, Wallace RE. Proc Soc Exp Biol Med 71, 196 1949. For use outside $CO_2$ incubators.
(25) Ham RG. Proc Nat'l Acad Sci U.S. 53, 288, 1965. Analogous to Tyrode's (9) Table I. $HCO_3$ deficient.
(26) Delbecco R, Vogt M. J Exp Med 99, 167-182, 1954. Simply Krebs Ringer Phosphate with lowered Ca and Mg. The high Pi would lower cellular [$\Sigma$ ATP]/[$\Sigma$ ADP] [$\Sigma$ Pi].
(26a) Delbecco R. Virology 8, 396, 1959. Lacks redox balance as does (22) and (25). The pH is high for general use.

Contemporarily, a large number of different aqueous electrolyte solutions or their salt concentrates are prepared sold in commerce, and used in in vitro fluids, principally as tissue culture fluid media.

Even a cursory examination of Table I will confirm the medical dicta that "plasma is an unmakable solution". The solutions listed in Table I illustrate this belief. The essential problem is that plasma contains, in addition to major inorganic electrolytes, trace quantities of various electrolytes plus various metabolites including plasma proteins. In practice, it has not been possible to construct synthetically a replication of plasma extracellular fluid or intracellular fluid because of their complexity. Blood, extracellular and intracellular fluid, and even plasma can be regarded as tissues.

In most prior art electrolyte solutions, the concentration of chloride anions ($Cl^-$) is higher than in human plasma or serum. For example, the Krebs-Henseleit solution (see Table I) contains a concentration of $Cl^-$ which is about 20% higher than in fluids such as plasma. This anion gap, that is, the difference between the positive cations and the negative anions, is now known to be due largely to the anionic metabolites such fluids plus the contribution of acidic amino acid groups found on plasma proteins. Referring to Table I, it is seen that the total positive cations in, for example, human plasma is 142-154 meq/l while the total anions is only about 128-137 meq/l leaving a deficit of about 14-17 meq/l of anions. For convenience, the anion gap in such fluids can be expressed as the ratio of sodium cation milliequivalents per liter to chloride anion milliequivalents per liter.

From Table I, it is clear that the Kreb's Serum substitute (Kreb's, H. A. *Biochem. Biophys. Acta* 4, 249-269, 1950) comes closest to approximating the electrolyte composition of such fluids. In such solution, Krebs attempted to correct the excessive $Cl^-$ content in Krebs Henseleit solution (*Hoppe. Z. Phusiol. Chem.* 210, 33-66, 1932) using metabolic experiments with tissue slices. Because of the law of electrical neutrality, $Na^+$ cannot be added to a solution without some anion (such as $Cl^-$) being added also; the sum of cations and anions must be equal in any solution. In his 1950 attempt, Krebs chose pyruvate$^-$, L-glutamate$^-$, fumarate$^{2-}$ as anions to be added.

The alternative to Krebs-Henseleit is essentially Krebs-Ringers Phosphate or Delbecco's tissue culture media where Pi is present in amounts about 10 to 25 times normal plasma concentrations. Such media are used so as to eliminate $HCO_3^-/CO_2$. Both such solutions, used respectively in perfusion or cell culture not only have too high Pi which induces an abnormal intracellular [$\Sigma$ATP]/[$\Sigma$ADP]/[$\Sigma$Pi] ratio but also have too low a Na:Cl ratio inducing hyperchloremic acidosis.

The alternate use of lactate$^-$ or pyruvate alone induces severe abnormalities in cellular redox state and phosphorylation potential. The use of gluconate$^-$ induces abnormalities in the hexosemonophosphate pathway. Indeed, all previously used organic ions violate the "safe entry points" or the normal Na:Cl ratio as herein defined.

In addition to the use of lactate, gluconate, fumarate, glutamate, pyruvate, and citrate anions in current commercially available prior art electrolyte fluids, and wherein such anions are typically employed at levels above those found in the (plasma or serum) of healthy humans, many such prior art commercial fluids also employ high levels of nonionic metabolites, such as fructose and glycerol, which induce separate redox state and phosphorylation potential abnormalities of their own. Thus, fructose causes severe abnormalities in phosphorylation potential with rapid destruction of liver purine nucleotides and their release into blood sometimes leading to renal shutdown due to uric acid deposition in the kidneys (see Woods, H. F., Eggleston, L. V., and Krebes, H. A. *Biochem. J.* 119, 501-510, 1970). Fructose in plasma above 0.2 mM must be considered to violate the "safe entry point". Likeiwse, use of intravenous glycerol at levels above 5 mM/l as currently practiced leads, in tissue containing glycerol kinase, such as kidney and liver, to accumulation of 10 mM glycerol phosphate (over 100 times normal). (See Burch, H. B. et al. *J. Biol. Chem.* 257, 3676-3679, 1982).

Mammalian systems normally operate at temperatures between about 37°-38° C. whereas, by common thermodynamic convention, neutral pH is taken to be about 7 at 25° C. It is clear that changes in pH, (the negative $\log_{10}$ of [$H^+$] concentration) necessarily affect the fundamental energetic relationships occurring in living cells. Also, enzymes have sharply defined ranges of [$H^+$] concentration in which they perform their catalytic functions in a normal manner. Deviation of mammalian plasma pH down to 6.9 or above 7.7 from its normal range of 7.35-7.45 is therefore fatal to most mammalian organisms. Massive changes in the cellular redox and phosphorylation states also disorder cellular homeostasis.

The pH of human plasma is normally maintained by the human body in the range from about 7.35 to 7.45 while the pH of human cellular cytoplasm is about 7.2 (see Veech et al. in *J. Biol. Chem.* 254, 6538–6547, 1979). If blood pH drops to 6.8 in man, then death ensues from cardiac arrest, and if blood pH increases to above pH 7.7, then death ensues from convulsions.

The major chemical system maintaining body pH within this narrow normal range is the $[CO_2]/[HCO_3^-]$ buffer system. The $[CO_2]$ of blood is maintained minute to minute by a portion of the mammalian brain called the respiratory center which senses brain cell pH and adjusts the depth and speed of respiration in response to changes in pH by increasing or decreasing $[CO_2]$ according to the famous Henderson Hasselbalch equation (Henderson, L. J. *Silliman Lectures, Yale U. Press, New Haven*, 1928).

Even though pH is thus seen to be a critical factor in mammalian blood, many commercial electrolyte solutions used in vitro attempt to maintain pH with phosphate or even artificial buffers such as Tris and the like. The absence of $CO_2/HCO_3^-$ necessarily induce profound changes in the $[NADP^+]/[NADPH]$ redox state but in all the metabolites of glycolysis (see Miller, A. L. et al. *J. Neurochem.* 25, 553–558, 1975).

The compositions and methods of the present invention overcome the above indicated prior art problems. These compositions and methods employ definite ratios of [bicarbonate$^-$]/[carbon dioxide], [l-lactate$^-$]/[pyruvate$^-$], and [d-betahydroxybutyrate$^-$]/[acetoacetate$^-$]. Each of these mixtures constitute a near equilibrium couple which is known to be a normal constituent of mammalian plasma. While each of these pairs of components has been previously employed at least on a laboratory basis in solutions used for animal (mammalian) experiments, these mixture pairs have never previously been used in an electrolyte solution to obtain a normal Na:Cl milliequivalent ratio or to solve the anion gap problem.

All previous electrolyte solutions, and plasma substitutes, induce severe and measurable pathogenic abnormalities and no prior art electrolyte solution or plasma substitute has both (a) employed at least one of the three mixture pairs of this invention and (b) achieved a normal Na:Cl milliequivalent ratio as taught herein. Thus, for example, the krebs-Henseleit solution contains the $[HCO_3^-]/[CO_2]$ buffer system (but contains excessive chloride ions9. Schimassek (Schimassek, H. *Bio. Chem. Z.* 336, 460, 1963) added about normal blood levels of lactate and pyruvate to what is essentially Tyrode's solution (see tyrode, M. J. *Arch. Int. Pharmacodyn* 20. 205, 1910) containing a 2.5% albumin in an attempt to create a physiological solution for perfusion. It should be noted that Schimassek added 1.33 mM/L D-L-lactate, which is definitely abnormal (see normal blood lactate levels shown in Table I). Further, the Na$^+$ of 151 mM/l ad Cl$^-$ of 147.5 mM/l in Schimassek's modified Tyrode's solution approximates the concentration of 155 mM/l Na and 155 mM/l Cl is so-called normal (0.9%) saline, the most widely used electrolyte infusion solution, and thus obtained a grossly abnormal Na:Cl milliequivalent ratio of 1.00. Normal plasma has a Na:Cl milliequivalent ratio of about 1.24–1.45 with a mean of about 1.38. Infusions of electrolyte solutions with a Na:Cl milliequivalent ratio of less than about 1.38 have long been known to cause hyperchloremic acidosis in the treated organism. (See Levinsky, N. G. in Harrison's *Textbook of Medicine* pp. 230–236, McGraw-Hill, N.Y., 1983). It is the attempt to avoid this problem that leads to the wide use of such solutions as Ringer's lactate or acetate dialysis fluids which overcome the Na:Cl ratio problem, but which in turn create gross abnormalities of other types. It is the attainment of a normal Na:Cl milliequivalent ratio in a manner which avoids the pathological consequences inherent in all currently known or practiced methods which is a major part of the invention herein disclosed.

The making of a Krebs-Henseleit electrolyte solution (or other prior art electrolyte solution) and the incorporation there into of a mixture of l-lactate and pyruvate anions, or of a mixture of d-betahydroxybutyrate and acetoacetate anions did not, and could not, result in the making of an electrolyte solution wherein the anion gap problem was overcome (or wherein the milliequivalent ratio of sodium cations to chloride anions was normalized), in accordance with the teachings of the present invention, because each of such resulting solutions would still contain excessive chloride anions and so would inevitably cause hyperchloremia if and when used under in vitro use conditions.

In general summary, the prior art describes a series of electrolyte solutions typically of about 270–320 milliosmoles (or higher) comprised of: (a) 1 to 4 metallic cations of sodium, potassium, magnesium, and calcium in amounts greater than 0.5 mL/L, (b) 1 to 5 inorganic anions of chloride plus also $H_2PO_4^- - HPO_4^{1-}$ (the later also called Pi herein), sulphate ($SO_4^{2-}$), (c) 0 to several organic carboxylic or bicarbonate anions, (d) 0 to about 12 nonionic materials in concentrations of greater than about 0.5 mL/L from the group comprising $CO_2$ gas, glucose, urea, glutamine, and others, and (e) sometimes one or more high molecular weight substances, such as albumin, hemocel, and the like. None of these solutions, for the reasons herein above explained, either normalize the milliequivalent ratio of Na:Cl at all, or normalize this ratio without causing profound and adverse physiological consequences. In the present invention, there are provided processes and compositions of a complex fluid nature for in vitro usage which can substantially completely eliminate all of such prior art problems. While the components of these new solution compositions are known solution components, no one has heretofore formulated the solutions of the present invention which not only tend to achieve a normal plasma milliequivalent ratio of sodium cations to chloride anions, but also tend to achieve a normalization of plasma pH and a normalization of the cellular redox state and the cellular phosphorylation potential. Also, these new solutions permit one to avoid usage of the previously employed carboxylic anions, such as acetate, or lactate alone, which cause adverse effects.

BRIEF SUMMARY OF THE INVENTION

This invention relates in one aspect to improved in vitro processes for accomplishing tissue culture perfusion and/or incubation of living animal cells, groups or cells, or organs, by contacting such cells with an aqueous solution wherein:

(a) the ratio of sodium cation milliequivalents per liter to the chloride anion milliequivalents per liter are so selected as to tend to produce the range found in normal animal intracellular fluid, and (b) there is a physiologically effective amount of at least one near-equilibrium couple selected from the group consisting of -
  (1) bicarbonate⁻ and carbon dioxide,
  (2) l-lactate⁻ and pyruvate⁻, and
  (3) d-betahydroxybutyrate⁻ and acetoacetate⁻, and
(c) the pH ranges from about 76.9 to 7.8.

This invention further relates to physiologically compatible aqueous electrolyte salt solutions for tissue culture or contacting animal mammalian cells in vitro in any manner, which solutions contain a ratio of sodium to chloride and which solutions incorporate at least one such near-equilibrium couple within the ranges specified to so achieve said specified Na:Cl ratio.

This invention provides electrolytes of the class indicated wherein physiologically normal concentrations of the divalent cations $Mq^{2+}$ and $Ca^{2+}$ may be included without precipitation.

When used for contacting mammalian or avian cells or organs in accord with the present process teachings, such a solution generally:
  (a) tends to maintain the intracellular mulliequivalent ratio of sodium cations to chloride anions in a normal range, and
  (b) tends normalize intracellular pH and/or tends to normalize the cellular redox state and the cellular phosphorylation potential.

In such in vitro applications as cell (including organis, embryos, and the like) perfusion, cell incubation, or the in vitro preservation of cells or of whole organs, as those skilled in this art will readily appreciate, it is possible to use the electrolyte solution of this invention as such for contacting purposes. In other such applications, the electrolyte solutions of this invention are typically used in combination with nutrients in the quantity generally of the types known and heretofore used in this art, as those skilled in this are will readily appreciate.

One (first) class of such solutions characteristically utilizes (contains) an inorganic class of anions comprised of chloride and bicarbonate. These solutions have a physiological pH which is broadly in the range from about 5 to 9, and preferably in the range from about 6.9 to 8.6, and more preferably in the range from about 7.35 to 7.45, and most preferable is about 7.4. When $HCO_3^-$ is present, dissolved carbon dioxide must be present in these solutions $CO_2$ must also be present in the amounts specified so as to achieve the pH desired. When used, these solutions not only tend to maintain a normal Na:Cl ratio in the surrounding fluid media, but also tend to set (regulate) the treated cells's internal (e.g., intracellular fluid) pH within normal limits of about 7.35 to 7.55.

Another (second) class (preferred) of such solutions characteristically utilized (contains) chloride anions and a class of carboxylate anionic couples comprised of at least one pair from the group consisting of (a) a mixture of l-lactate⁻ anions and pyruvate⁻ anions, (b) a mixture of d-betahydroxybutyrate⁻ and acetoacetate⁻ anions, and (c) a mixture of both (a) and (b). These solutions have a physiological pH which is as above defined in connection with such (first) class of solutions. When administered, these solutions not only tend to maintain the treated cells redox state within a normal range, but also tend to maintain that cells phosphorylation potential within a normal range.

Another (third) class (more preferred) of such solutions characteristically utilized (contains) both chloride anions, and bicarbonate/carbon dioxide mixture, as in such (first) class of solutions, but also utilizes (contains) such class of carboxylate anionic couples, as in such (second) class of solutions. When administered, these solutions achieve the above indicated effects obtained from the use of such (first) class of solutions and the above indicated effects obtained from the use of such (second) class of solutions.

The specified milliequivalent ratio of sodium to chloride in normal mammalian blood generally is believed to be in the range from about 1.28:1 to 1.45:1. Broader rages of ratios centering around these ratios are employed in solutions used in the practices of this invention although marked deviations from the normal ranges may also be used to achieve special purposes.

The total quantity, or sum (sigma), of bicarbonate anions and carbon dioxide present in a solution of this invention ranges from 0 to about 55 millimoles per liter of solution. The ratio of bicarbonate milliequivalents per liter to dissolved carbon dioxide milliequivalents per liter in a solution of this invention can range from about 6.3:1 to 55:1.1. Preferably, bicarbonate concentration ranges from about 20 to 50 mM/l and such ratio ranges from about 10:1 to 32:1, and more preferably such total ranges from about 23 to 35 mM/l while such ratio ranges from about 19:1 to 21:1. A ratio of 19.95 for $[HCO_3^-]/[CO_2]$ gives a pH 7.4 which is presently particularly preferred.

The total quantity, or sum (sigma) of l-lactate anions and pyruvate anions present in a solution of this invention ranges from 0 to about 55 millimoles per liter of solution. The ratio of L-lactate anion milliequivalents per liter to pyruvate anion milliequivalents per liter in a solution of this invention can range from about 30:1 to 1:1. Preferably, such total quantity ranges from about 0.5 to 10 mM/l and such ratio ranges from about 3:1 to 15:1, and more preferably such total quantity ranges from about 2 to 8 mM/l while such ratio rages from about 5:1 to 12:1.

The total quantity, or sum (sigma) of d-betahydroxybutyrate anions and acetoacetate anions present in a solutions of this invention ranges from about 0 to about 55 millimoles per liter of solution. The ratio of D-betahydroxybutyrate anion milliequivalents per liter to acetoacetate milliequivalents per liter in a solution of this invention can range from about 6:1 to 0.5:1. Preferably, such total ranges from about 0.5 to 10 mM/l and such ratio ranges from about 4:1 to 1:1, and more preferably such total ranges from about 2 to 5 mM/l while such ratio ranges from about 3:1 to 1.5:1.

By the term "milliequivalent ratio" as sometimes used herein, reference is made to the ratio of milliequivalents per liter of one substance to milliequivalents per liter to another substance in an aqueous medium.

One of the three near-equilibrium couples employed in the practice of this invention (the bicarbonate⁻/carbon dioxide couple) generally tends, as used in this invention, to regulate the concentration of hydrogen ions in the bathing media and in treated cells, and each one of such couples generally tends to normalize the redox state of each of the three pyridine nucleotide couples. The phosphorylation potential also generally tends to be normalized. Also, each such near-equilibrium couple when used as herein described constitutes a safe entry point into the metabolic system of a treated cell.

By the term "safe entry point" as used herein reference is generally had to a metabolite which, in living tissue or cells:
(1) does not cause a massive build up of one or more of intermediate cellular metabolites,
(2) does not cause a severe disruption of any one of the controlling nucleotide ratios in a living cell,
(3) can be added to a physiological system of a living mammal at a concentration level which is greater than that which is found normally in resting, overnight fasted normal man (such as blood plasma of a fasting mammal) without causing appreciable distortion in metabolism and without causing appreciable pathological conditions to arise, and
(4) may be found in normal variants of the physiological state as when the total of D-betahydroxybutyrate plus acetoacetate reaches a level of about 7 to 10 mM/l in three-day fasting man, or the total of L-lactate plus pyruvate rises to a level of about 5 to 6 mM/l in a normal jogging man.

Further, each such above described near-equilibrium couples in this invention exhibits a distribution or permeability between intracellular fluid and extracellular fluid such that the ratio of the concentrations in, respectively, intracellular fluid to extracellular fluid ranges from about 1.0:1 to 1.5:1 in most all mammalian cells.

Nonionics incorporated with the solutions of this invention preferably should each constitute a safe entry point. For example, glucose above 13 mM/l is higher than ever occurs under normal physiological conditions in a healthy man. Use of a glucose above 13 mM/l (as in the widely used 5% glucose solution) as a calorie source is, apart from consideration of the source of pathology, and apart from the carboxylate couples, considered herein to be an acceptable source of calories. The extreme ability of the mammalian body to regulate of glucose metabolism makes it far to be preferred over other possible nonionics, such as fructose or glycerol, which enter the metabolic system in an un-controlled manner causing pathologic changes such is already referenced, and so such are not safe entry points.

In the special cases where tissue water may need to be removed, as in the case of cryo-preservation of tissues, very high concentrations of osmotically active substances may be used.

Characteristically, a solution used in the practice of this invention contains from about 130 to 170 millimoles per liter of sodium cations, and more preferably from about 129 to 163.5 mM/l and most preferably from about 136 to 155 mM/l. In addition, a solution contains sufficient chloride anions to produce a milliequivalent ratio of sodium cations to chloride anions in the range above defined.

Optionally, in addition to sodium, a solution of this invention contains at least two of the following additional metallic cations each in a respective quantity as below indicated:

| cation component | Quantity range (millimoles per liter) | |
|---|---|---|
| | broad | preferred |
| potassium | 0–40 | 1–5 |
| calcium | 0–10 | 0.2–1.5 |
| magnesium | 0–10 | 0.2–1 |

Optionally a solution of this invention can have additionally incorporated (dissolved) therein from 0 to about 6000 millimoles per liter of at least one substantially nonionic (including zwitterionic) osmotically active substance (which is preferably metabolizable).

A solution used in the practice of this invention is further characterized by generally having
(1) sufficient total substances dissolved therein to produce an osmolarity ranging from about 260 to 6400 milliosmoles (mOs), and preferably from about 265 to 550 mOs, and most preferably from about 280 to 320 in mOs;
(2) the relationship between total (dissolved) substances is such that the pH ranges from about 6.8 to 7.8; and most preferably from about 7.35 to 7.55;
(3) the charges of all cations equal the charges of all anions, and
(4) the minimum total concentration of all such near-equilibrium couple(s) present is at least about 0.1 millimoles per liter, and preferably is at least about 0.5 mM/l, and more preferably about 2 mM/l, while the maximum concentration thereof is preferably not more than about 80 and more preferably is not more than 61 mM/l and most preferably is not more than about 50 mM/l.

Examples of usable such nonionic substances include glucose, glycerol, fructose, sorbitol, urea and the like. Glucose is presently most preferred for nutritional purposes, and glycerol presently most preferred for cryopreservation purposes. Also optionally a solution of this invention may have incorporated in it from 0 to 55 mEq/liter of a polyanion incorporated in it, preferably in the Na form.

As hereinbelow explained, the processes and the solutions of the present invention find use in a wide variety of in vitro uses, such as "balanced salt solutions" (see Table III) to which nutrient mixtures may be added, perfusion fluids for organs, perfusion fluids containing substances like glycerol or urea for cytopreservation of organs, cell incubation experiments, and the like.

Various additional objects, aims, purposes, features, advantages, applications, variations, and the like will be apparent to those skilled in the art from the teachings of the present specification taken with the claims.

DETAILED DESCRIPTION

This description is based upon best available information (including theory) known to the inventor. Any misdescription or the like, if such should exist, is not believed to alter the fundamentally correct basis and evidence supporting the present invention.

A. The Redox State

In biological cells, most reactants are catalyzed by enzymes of which an average cell may have of the order of $10^4$. In one classification, enzymes may be grouped in only six major functional categories:
(1) dehydrogenases which transfer $H^+$ and $e^-$ from one substrate to another by the use of co-factors, such as $NAD^+$ (nicotinamide adenine dinucleotide), or prosthetic groups, such as FAD (flavin adenine dinucleotide), or others;
(2) kinases or phosphotransferases which effect the group transfer of a phosphate to a substrate usually by using a co-factor, such as ATP or other similar phosphate-containing compounds;
(3) carbon-carbon bond group transferases which either make or break carbond-carbon bonds using co-factors of the coenzyme type or occur on a solid state matrix, such as the glycogen particle, or the surface of a fatty acid synthase multi-enzyme complex;

(4) isomerases which effect internal rearrangements within a compound;

(5) hydratases which either add or subtract water from a substrate and (6) peptidases which break C—N bonds or create such bonds again usually taking advantage of a solid state synthetic matrix, such as a ribosome.

A special class of substrates taking part of biological reactions catalyzed by enzymes are called so-factors or co-enzymes. Co-enzymes, such as, for example, NAD, become attached and detached from an enzyme during a catalytic cycle, while prosthetic groups, such a flavin nucleotides or cytochromes, remain firmly attached during the catalytic cycle.

Since co-enzymes take part in multiple intracellular reaction within a given cellular compartment, the chemical potential of the co-enzyme couple becomes of central importance in energy transformation and oxido-reductions occurring in living matter. The thermodynamic characteristics of a particular whole set of oxido-reduction reactions is dependent upon the ratio of the free concentrations (strictly speaking, the activities) of the free [NAD+] and free [NADH] ratio. The ratio [NA(P)D+]/[NAD(P)H], thus represents and defines the redox state, at a given pH, of a particular pyridine nucleotide couple, and this ratio then determines:

(1) the extent and direction of reversible reactions in near-equilibrium with that coenzyme couple;

(2) the extent to which a co-enzyme couple can be effective as an intracellular reducing agent, for example, in reducing the beta-oxoacyl co-enzyme A to beta-hydroxyacyl-coenzyme A; and (3) the magnitude of the free energy changes of oxido-reductions in the electron transport chain responsible for the major portion of ATP synthesis.

The term "redox state" as thus used herein can be considered to refer to the oxidation-reduction state of any one or more of the three main pyridine nucleotide couples. Each of these couples are:

(A) The cytoplasmic [NAD+]/[NADH] linked dehydrogenase reactions of: (1)1-Lactate dehydrogenase (EC 1.1.1.27); (2) Malate dehydrogenase (EC 1.1.1.37); and (3) Glycerol-3-phosphate Dehydrogenase (EC 1.1.1.8).

(B) The mitochondrial [NAD+]/[NADH] linked dehydrogenase reactions of: (1)d-Beta-hydroxybutyrate dehydrogenase (EC 1.1.1.30); and (2) Glutamate dehydrogenase (EC 1.4.1.3).

(C) The cytoplasmic [NADP+]/[NADPH] linked dehydrogenase reaction of: (1) 1s-Isocitrate dehydrogenase (EC 1.1.1.42); (2) 6-Phosphogluconate dehydrogenase (EC 1.1.1.44); and (3) the Malic Enzyme (EC 1.1.1.40).

The three pyridine nucleotide couples or pools each achieve different redox potentials because of the chemical energies of the substrates to which they are linked by their respective enzymes since the standard redox potential of [NAD+]/[NADH] is about −0.32 V. Thus, the near-equilibrium NAD-linked dehydrogenases have a Keq of about $10^{-11}$M, the mitochondrial NAD-linked dehydrogenases have a Keq of about $10^{-9}$M, and the cytoplasmic NADP linked dehydrogenases have a Keq of about 1. The difference in pyridine nucleotide redox states within the cell may be considered to result from the fundamental properties of matter. Over time, enzymes have evolved which take advantage of these fundamental properties to organize the chemical reactions of the cell into coherent purposeful sequences we nown as metabolism.

The oxidation of 1-lactate anions to pyruvate anions (that is, the losss of 2H+ and 2e− from lactate) is accompanied by the reduction of pyridine nucleotide NAD+. That is, NAD+ gains two electrons and one H+ being liberated into the aqueous media where its activity is indicated and controlled by the $HCO_3^-/CO_2$ couple.

In general, the term "redox state" may also be defined as a ratio of [oxidized substrate]/[reduced substrate]. The half or mid point potential $E_h$ is conventionally measured as a potential in volts relative to a standard hydrogen electrode potential in accordance with the Nernst equation. The mid-point potential of the NAD+ system, that is, where the ratio of [NAD+]/[NADH] equals 1 at a pH of 7.0 and a temperature of 25° C., is −0.32 volts under standard conditions. The cytoplasmic pyridine nucleotide system accepts H+ and e− from the organic compounds provided to mammalian organisms and transfers them to the mitochondrial pyridine nucleotide system where, by the electron transfer system, the 2H+ + 2e− reduce ½ $O_2$ to form water while conserving the energy of the oxidation reduction reaction by converting AD+Pi to ATP. The reaction generates energy and heat. The redox state of cytoplasmic [NAD+]/[NADH] couple is about −0.19 volts, that of the mitochondrial [NAD+]/[NADH] couple is about −0.28 volts while that of the cytoplasmic [NADP+]/[NADPH] couple is about −0.42 volts. The last of NADP+ couple is a much stronger reducing agent than the others and is used for reductive synthesis in the body, such as the making of fatty acids from carbohydrates; (see Krebs and Veech, 1969) in *The Energy Levels and Metabolic Control in Mitochondria* (Papa, S., Tayer, J. R., Quagliariello, E. & Slater, E. C., eds) pp 329–382, Adriatica Edrice, Bari.

In the case of a living cell, a plurality of oxidation-reduction reactions occur simultaneously. Under normal conditions, these reactions occur in a normal healthy cell in a predictable manner. How these various redox states are regulated has just been described in thermodynamic terms. The normal healthy cell keeps the redox state of its free cytoplasmic [NAD+]/[NADH] redox couple at a ratio of about 500 to 1500 which corresponds to a voltage of about −0.2 volts. In this way, the cytoplastic pyridine nucleotides can accept the H+ and e− from the substrates or food presented into energy. When the cell is metabolizing very reduced substrates, such as fatty acids, the cytoplasmic [NAD+]/[NADH] is about 400–800. When the cell is metabolizing carbohydrates or amino acids, it is obvious that these compounds are already partially oxidized. Therefore, the free cytoplasmic [NAD+]/[NADH] reflects the oxidation level of its substrate and becomes more oxidized in the range of about 800 to 1500.

The redox state of the free cytoplasmic [NAD+]/[NADH] couple can be determined by various techniques, such as by measuring the ratio of [1-lactate−]/[pyruvate−] (a) in freeze clamped tissue, (b) in the venous effluent leaving the organ in question, or (c) in the medium bathing the tissue in question. Alternatively [1-malate−]/[oxaloacetate−] or [α-glyerophosphate/-dihydroxyacetone-P] ratios in tissue may be measured, if desired. The value of cytoplasmic [NAD+]/[NADH] can the be calculated.

In healthy living mammals, the ratio of [1-lactate−]/[pyruvate−] is about 6, but can range, under special situations, such as starvation, to about 15-20. A [1-lactate⁻]/[pyruvate⁻] ratio below about 20, as occurs after ethanol consumption because of its links to the cytoplasmic [NAD+]/[NADH], is pathologic. A characteristic in all cells having a low [NAD+]/[NADH] ratio is believed to be demonstrable (observable) pathologic consequences, such as tissue swelling, low phosphotylation potential, low plasma membrane voltage, and abnormal electrolyte distribution between intracellular and extracellular $H_2O$.

Similarly, the redox state of the free mitochondrial [NAD+]/[NADH] can be determined by various techniques using tissues such as, for example, kidney or liver, by measuring the ratio of [d-beta-hydroxybutyrate⁻]/[acetoacetate⁻] (a) in freeze-clamped tissue, (b) in the venous effluent leaving such tissue, or (c) in the fluid bathing isolated such tissues. A determination of the free mitochondrial [NAD+]/[NADH] in other tissues, such as brain or heart muscle, is more complex, but, in some cases, can be accomplished by measurement in freeze clamped tissue of the [alpha-keto glutarate⁻][$NH_4^+$]/[glutamate⁻] ratio (see Miller A. L., Hawkins, R. A., and Veech, R. L. *J. Neurochem.* 20, 1393–1400, 1973).

The normal ratio of mitochondrial [NAD+]/[NADH] is between about 5 and 20, and the normal ratio of [betahydroxybutyrate⁻]/[acetoacetate⁻] is about 1.3 to 5. The value of mitochondrial [NAD+]/[NADH] can then be calculated.

The redox state of the free cytoplasmic [NADP+]/[NADPH] couple is, of course, affected by the [$CO_2$] of surrounding fluids. Because of the lack of substrates which are permeant to the cell wall without significant and variable gradients, this redox state cannot at present be directly and totally regulated other than by the intracellular metabolic links with the cytoplasmic and mitochrondrial [NAD+]/[NADH]. (See Krebs H. A. and Veech, R. L. "Pyridine Nucleotide Interrelations", 1969 in *The Energy Level and Metabolic Control in Mitochrondrial* in Papa, S., Tager, J. M., Quagliariello, E., and Slater, E. S., EDS, pp 329-383, Adriatica Editrice, Bari). Thus, for instance, because pyruvate reacts in both cytoplasmic [NAD+]/[NADH] and [NADP+]/[NADPH], administration of [$HCO_3^-$]/[$CO_2$] and [1-lactate⁻][pyruvate⁻] within certain narrow limits regulates these ratios because:

$$\frac{[NAD_c^+]}{[NADH_c]} = \frac{[NADP_c] \times K_{malic\ enzyme} \times [malate^{2-}]}{[NADPH_c]\ K_{LDH}\ [\text{1-lactate}^-]\ [CO_2]}$$

Pyruvate⁻, 1-lactate⁻ and $CO_2$ are permeable to cell wall in a simple fashion, as are d-betahydroxybutyrate⁻ and acetoacetate⁻, while malate²⁻ and other dicarboxylates are not.

While the importance of redox state to the maintenance and normalization of intracellular metabolic processes and bioenergetics has long been recognized, there has never been previously so far as is now known any attempt to regulate or to normalize the redox state in cells being manipulated in vivo using electrolyte solutions which contain a normal Na:Cl ratio. The present invention provides compositions and methods for regulating and/or normalizing the redox state in cells or portions of organs or whole organs or whole organisms being manipulated or grown in vitro.

Existing electrolyte fluids make no attempt to maintain or normalize cellular redox potentials in any way whatsoever. In fact, most existing electrolyte fluids for in vitro use actually severely distort or make abnormal the redox balance of the cells, resulting in multiple and definable abnormalities. In this way, existing electrolyte fluids distort such things as, for examples, the rate of fat oxidation, the rate of glucose production, the rate of uric acid excretion, the rate of galactose metabolism and the like. All of these abnormalities lead to, pathological consequences of a definable type such as, for example, in liver.

B. The Phosphorylation Potential

Just as the [NAD+]/[NADH] ratio is defined as a "redox state", by analogy, it is customary to define the energy state of the adenine nucleotide co-enzyme couple as the "phosphorylation state" or the "phosphorylation potential". Because in living cells ATP, ADP, the $HPO_4$ exist in several charged forms, and in various complexation states with $Mg^{2+}$, it is customary to define these forms as sigma ATP, sigma ADP, and sigma Pi. The phosphorylation potential is thu defined by the relationship [sigma ATP]/[sigma ADP][sigma Pi].

It is clear that the reaction of oxidative hoshorylation contans both the redox state of mitochondria and the cytoplasmic phosphorylation potential. While the phosphorylation potential cannot apparently be controlled by addition of ATP or ADP to the media surrounding cells because these compounds are impermeant to cell wall directly. There is, however, another reaction which is in near-equilibrium with the cytoplasmic [sigma ATP]/[sigma ADP][sigma Pi] (see Veech et al. in *J. Biol. Chem.* 254, 6538-6547, 1979). This reaction involves the two most active enzymes in the glycolytic sequence found in nearly all living cells and catalyzed by the enzymes glyceraldehyde 3-phosphate dehydrogenase (EC 1.1.1.29) and 3-phosphoglycerate kinase (EC 2.7.2.3). Veech et al. (reference just cited) provide an equation which defines the relationship between the free cytoplasmic phosphorylation state of [sigma ATP]/[sigma ADP][sigma Pi]. This relationship is now and accepted by those familiar with this art and is (equation 5):

$$K_{G+G} = \frac{[\text{sigma3PG}]}{[\text{sigmaGAP}]} \cdot \frac{[\text{sigmaATP}]\ [\text{NADH}]\ [H^+]}{[\text{sigmaADP}]\ [\text{sigma Pi}]\ [NAD^+]} =$$

$$1.83 \times 10^{-4}$$

$$\frac{K_{G+G}}{K_{LDH}} = \frac{[\text{sigma3PG}]}{[\text{sigmaDHAP}]/22} \cdot \frac{[\text{sigmaATP}]}{[\text{sigmaADP}]\ [\text{sigmaPi}]} \cdot$$

$$\frac{[\text{lactate}]}{[\text{pyruvate}]} = 1.65 \times 10^7 M^{-1}$$

Metabolism in any living cell may be considered to be an ordered process whereby [H+] and electrons [e⁻] are removed from substrates and passed to co-enzyme acceptors which are largely cytoplasmic NAD+. This co-factor thus has a potential in the cell far more oxidized at about −0.19 volts than its standard potential of about −0.32 volts so that it may accept these electrons. The H+ and e⁻ gathered in the cytoplasm, or even created in the mitochondria, may then be transferred to mitochondria by mechanisms involving other substrates linked to mitochondrial [NAD+]/[NADH], which has a lower potential of about −0.28 volts in most mammalian cells. If e⁻ and H+ are produced with a higher voltage, such as for example, from the oxidation of succinate or fatty acids, they form reduce $FADH_2$ from FAD which has a more oxidized potential and therefore less potential energy. H+ and electrons produced from NADH-linked substrates produce 3 ATP for each $\frac{1}{2}$ $O_2$ consumed while those from flavoprotein (FAD) acceptors produce only 2. This difference in energy is due to the fundamental difference in the chemical reactions involved in producing the H+ and e−.

The fundamental process of cell respiration where NADH is oxidized to form heat and energy is called oxidative phosphorylation. It occurs in cellular organelles called mitochondria in a series of redox reactions called the electron transport chain. The mitochondrial electron transport system takes two electrons [2e−] from substrates and passed them up the chain to reduce $\frac{1}{2}$ $O_2$ forming $H_2O$. The energy realized in this process is conserved in the cell in a chemical form of the anhydride bond in the terminal phosphate group of adenosine triphosphate (ATP). The formation of three pyrophosphate bonds of ATP leads to the formation of $H_2O$ and requires 3H+ in addition to the formation of the 1 $H_2O$ formed from NADH plus H+ plus 2e− taken from the substrates being oxidized by the cell. The reaction of oxidative phosphorylation is a spontaneous one (see Veech et al. in cited reference).

The phosphorylation potential of living cells can be measured by determining the cellular contents of the components of certain metabolites (see Veech, R.L., in *J. Biol. Chem.* 254, 6538–6547, 1979). In certain tissues, such as brain, heart, or skeletal muscle, measurement of the components of the creatine kinase reaction (E.C. 2.7.3.2) may be used as the preceding reference describes.

Since on theoretical grounds Veech et al. in J. Biol. Chem. 254, 6538–6547, 1979, showed that [creatine]/[creatine-P] is in near-equilibrium with the cytoplasmic [sigma ATP]/[sigma ADP], it follows that the phosphorylation potential in skeletal muscle or brain may be evaluated in living cells by measuring the [sigma CrP]/[sigma Pi] ratio without resorting to freeze-clamping of the cells by the use of $^{31}P$ NMR (nuclear-magnetic resonance) as has been done by Chance and others (see Chance, B. et al. *Proc. Nat'l. Acad. Sci., U.S.* 78, 6714–6718, 1981). The agreement between the necessarily destructive methods heretofore used in animals by Veech, and the somewhat less precise but nonharmful methods of sigma creatine-P sigma Pi measurements with 31P NMR, demonstrate that the normal value of the phosphorylation potential or [sigma ATP]/[sigma ADP][sigma Pi] as estimated by Veech is essentially correct (as stated above). Further, the increasing availability of $^{31}P$ NMR facilities in academic medical centers ensures that measurements in living cells, organs or whole organisms being treated in vitro can be conducted without harming them.

Because the cytoplasmic [sigma ATP]/[sigma ADP]-[sigma Pi] or phosphorylation potential is related to the cytoplasmic [NAD+]/[NADH] or redox state by a near-equilibrium reaction catalyzed by glyceraldehyde-3-phosphate dehydrogenase and 3-phosphoglycerate kinase, it is possible to alter and regulate and normalize the phosphorylation potential of a living cell by affecting its redox state (as is believed to be accomplished in the present invention).

If a simple, reliable chemical means were known and/or could be devised to change the intracellular redox state, it would of necessity have to change the other components of the reaction which include the phosphorylation potential and would be of obvious fundamental importance in medicine and in many other related fields of biochemistry, physiology, molecular biology, tissue culture, veterinary medicine, and like endeavors. Such a chemical means is provided by the teachings of the present invention.

C. Redox Active Metabolites

As above indicated, a large portion of metabolism is devoted to energy generation which involves the removal of H+ and e− from substrates in cytoplasm or mitochondria for delivery to mitochondrial electron transport scheme for conversion of 2H+ plus 2e− with $\frac{1}{2}$ $O_2$ to yield $H_2O$ with the liberation of about 1 volt or 54 Kcal/mole of energy which is conserved in the [sigma ATP]/[sigma ADP][sigma Pi] couple. In mammalian and other cells, the [sigma ATP]/[sigmaADP]-[sigma Pi] has a delta G (free energy in calories per mole) of between −13.6 and −14.1 Kcal/mole. The transfer of this H+ and e− is accomplished by a series of cofactors, the major one being NAD (nicotinamide adenine dinucleotide) and its phosphate (called NADP). Oxidation is defined as the removal of electrons, and reduction as the addition of electrons. The removal or addition of e− plus H+ from substrates is catalyzed by enzymes, the major group of which are called dehydrogenases, as indicated above. The enzymes (catalysts) control the rates at which reactions occur, but the extent and the direction of a reaction, and the amount of energy (delta G) which may be liberated by a reaction, is determined by the inherent energy in the chemical bonds (delta G°) and the concentrations of the reactants and products.

Determination of any redox or energy state must always involve a ratio of chemical compounds, [product]/[reactant] and [oxidized co-factor]/[reduced co-factor]. The overall reaction is thus comprised of two individual redox systems, one of which is oxidized, while the other is reduced.

Those enzymes within a cell which are of sufficiently high activity relative to the flux through the enzyme to catalyze a state of near-equilibrium are suitable for controlling the redox state. A reaction may be experimentally determined to be in a state of near-equilibrium by measuring the equilibrium constant ($K_{eq}$) under conditions which approximate those existing within a cell, that is, where the ionic strength I equals 0.25, the pH equals 7 to 7.2, the temperature equals 38° C., and the free [$Mg^{2+}$] equals 0.5 to 1 mM, and also where I equals $\frac{1}{2}$ sigma molarity of ions times the valence of ions. With knowledge of the value of $K_{eq}$, the concentration of the reactants in a tissue may be measured in rapidly frozen tissue. If the value of [product]/[reactant] measured, in several couples gives the same co-factor ratio; then the reaction is said to be in "near-equilibrium". In the case of near-equilibrium dehydrogenase reactions, addition of a predetermined amount of a ratio of [product]/[reactant] allows one to set the [NAD+]/[NADH] ratio within the cell at a predetermined level provided the reactants penetrate the cell wall freely or in a constant ratio one to another. The redox state of [NAD(P)+]/[NAD(P)H] ratio may be set inside a cell by setting one or both of the [NAD+]/[NADH] ratios and controlling the [$CO_2$] with the range of 1.2–1.9 mM as stated in the preceding equation. Inclusion of [$HCO_3^-$]/[$CO_2$] in the bathing fluid at predetermined amounts controls pH in the media and within the cells.

Various cytoplasmic and mitochondrial NAD-linked dehydrogenase appear to be capable of controlling or setting the [NAD+]/[NADH] ratio in each of cytoplasm and mitochondrium. However, only the enzymes LDH (L-lactate dehydrogenase or E.C. 1.1.1.27), or D-B-hydroxybutyrate dehydrogenase possesses permeant metabolites capable of directly and completely regulating intracellular redox states in most cells. For example, one member or the other of such a redox couple may not be capable of permeating or penetrating a cell wall without a severe gradient in concentration being present. In other instances, one or the other of the partners of a redox couple when given above as is currently practiced in the art would lead to demonstratable toxicity when administered to a cell.

The near-equilibrium redox active metabolite carboxylate couples employed in the practice of the present invention, specifically, l-lacetate$^-$/pyruvate$^-$ and d-betahydroxybutyrate$^-$/acetoacetate$^-$, constitute safe entry points and appear to be unusual in their ability to not only normalize the redox state in cytoplasm through the reaction of l-lactate and pyruvate with LDH, but also to regulate the redox state in the mitochondrial through reaction of and D-betahydroxybutyrate$^-$ and acetoacetate$^-$ with the enzyme d-betahydroxybutyrate dehydroenase (E.C. 1.1.1.30) which is apparently present in most tissues at a high enough activity to maintain near-equilibrium conditions at most times.

As indicated above (see Table I and related text), previous attempts to normalize the sodium to chloride milliequivalent mole ratio of about 1.36 were usually done in vivo by adding either lactate, pyruvate or acetate alone, or a combination of lacetate and acetate, or other inappropriately paired carboxylate anions, leading inevitably in all known instances to severe and measurable pathological consequences. Such an attempt to normalize the Na:Cl ratio in in vitro solutions, such as perfusion or tissue culture, has previously been attempted by Krebs in his serum substitute where he used a combination of glutamate$^-$, fumarate$^{2-}$, and pyruvate$^-$. (Krebs HA. B.B.A. 4, 249, 1950) Such a combination led to severe tissue swelling due to abnormal uptake into the cell of Na glutamate and pyruvate led to pathological distortion of the redox and phosphorylation state. No other attempt to control the Na:Cl ratio in vitro is known to us.

In the solutions of the present invention, one employs at least one of three different near-equilibrium couple mixtures. In each couple mixture, the two member components are employed in a definite milliequivalent ratio relative to one another. Such a ratio is needed in order to control either the plasma pH, or the redox state (and consequently the phosphorylation potential), or both.

Among the possible mixture couples which could be used, these three couples were selected because, for each couple:

(1) The distribution of ions between extracellular fluid and intracellular fluid is predictable in all normal and pathological states.
(2) It is capable of achieving and regulating a predetermined redox state and for the phosphorylation potential within most living cells.
(3) At least one member thereof contains an anionic charge.
(4) It can be given in aqueous solution form so that the total levels administered do not substantially exceeds total levels found under normal physiologic conditions in mammalian blood (plasma).
(5) Both members thereof constitute safe entry points which enter the metabolic sequence and pathways at a safe entry point and these safe entry points, are at dead end terminals in the metabolic pathways, thus avoiding any possibility of a pathologic build up of metabolites with the consequence that a disordering of cellular metabolism would consequently result.

When solution levels of, respectively, l-lactate/pyruvate, d-betahydroxybutyrate/acetoacetate, and bicarbonate/$CO_2$ in the bathing fluid are maintained within their normal limits, then the redox state, the phosphorylation state, and the pH of fluids and cells each tend to be normalized which is achieved as a result of the use of such solutions.

Intracellular concentrations of each member of each couple is achieved through the extracelluloar fluid because each of the monovalent anions chosen, namely, l-lactate and pyruvate, D-betahydroxybutrate, and acetoacetate, and also bicarbonate, distribute themselves between extracellular water and intracellular water in concentration ratios or gradients which are the inverse of the hydrogen ion, thereby achieving a gradient or ratio of about 1.35 between extracellular and intracellular fluid. The nonionic dissolved $CO_2$ distributes itself substantially equally between extracellular fluid and intracellular fluid.

Those learned in the art realize a redox state must be defined at a certain pH, or [H$^+$] ion concentration. The near-equilibrium couple [HCO$_3^-$]/[CO$_2$] defines the ceklular pH or [H$^+$] concentration. This near-equilibrium couple is therefore an integral part of the redox state. Preferably the level of sigma [HCO$_3^-$] plus [CO$_2$] present in any given solution of this invention may vary under normal physiological conditions from about 10 mM/l to 55 mM/l, but in general, is (when present) in the range from about 25 to 35 mM/l. The milliequivalent ratio of [HCO$_3^-$]/[CO$_2$], of course, in effect, is defined so as to give a [H$^+$] ion concentration, or pH, in the physiological range as defined above.

The redox and phosphorylation states in various tissues in the rat have been given by Veech et al. *J. Biol. Chem.* 254, 6538–6547, 1979 and for the redox states in Veech, Eggleston and Krebs, *Biochem. J.*, 115, 609, 619, 1969. The same general principles are believed to hold for most mammalian and avian cells. NMR measured estimates of the phosphorylation potential in brain and muscle in living humans, agree well with these figures derived by freeze-clamping procedures.

By the term "plasma" or "blood plasma" as used herein, conventional general reference is had to the liquid part of the blood as distinguished from the corpuscles. Plasma can be prepared by various techniques well known to those familiar with this art typically using centrifugal force to separate a supernatant (which is plasma) after non-coagulated blood is centrifuged.

By the term "extracellular fluid" as used herein conventional general reference is had to all body fluids in extracellular spaces outside of the circulatory system (e.g. the blood) and outside of intracellular fluid in a mammal (typically constituting about 15% of the weight of a mammal).

By the term "intracellular fluid" as used herein conventional general reference is had the fluid within cells which constitutes about 57% of total mammalian body weight.

It is well known that (see Black, *Lancet* i, 305–312 and 353, 1953) infusions into a mammal of large amounts sodium and chloride in a solution milliequivalent ratio of 1 to 1 lead inherently to hyperchloremic acidosis. This knowledge lead to the development of such well known solutions as Krebs serum substitute (B.B.A. 1950) lactated Ringers, and also to the compositions used and in most dialysis solutions, wherein, in a majority of cases, the sodium to chloride milliequivalent ratio is normalized compared to plasma values by the addition of various organic anions (as described above). These organic anions chosen in the prior art areas described above. In no known prior art case, however, were any solutions with a normalized Na:Cl milliequivalent ratio produced which did not use organic ions in such a way as to inherently lead to severe and measurable metabolic abnormalities and pathologic consequences. Mixtures of redox pairs and of $HCO_3^-/CO_2$ were not used to normalize the Na:Cl ratio nor were the reasons known why a choice of near-equilibrium matched couples was desirable. Correction of this ratio between sodium cation and chloride anion by the mixture couples as taught by the present invention eliminates the pathologic consequences of all the prior art electrolyte solution compositions. In addition, the solution compositions of this invention tend to normalize fluid inorganic electrolyte composition including the divalent cations $Ca^{2+}$ and $Mg^{2+}$ and to correct the anion gap which in many instances could not be accomplished by prior art electrolyte solutions.

Thus, in summary, the compositions of this invention tend to normalize (a) fluid pH, (b) composition of major fluid inorganic electrolytes, (including the milliequivalent ratio of Na:Cl and the anion gap), (c) the redox state, and (d) the phosphorylation potential. These normalizations are obtained and achieved without the abnormal, pathological consequences inherent in all known art solutions. No other man-made solutions are presently known which will accomplish this combination of results.

D. Other Possible Benefits (Theorized)

It is theorized, and there is no intent to be bound by theory herein, that the solutions of the present invention, in addition to the properties above described, further tend to normalize at least one of the following states:

(1) Distribution of water between intracellular and extracellular compartments,
(2) Distribution of major inorganic electrolytes between intracellular and extracellular fluid,
(3) Transmembrane cellular potential, and
(4) The degree of organization within the cell or its entropy.

The ratio of the chemical activity of water on each side of the typical normal mammalian cell membrane is always unity. Movement of water across such a cell membrane is achieved by the movement of osmotically active substances. Changing the cellular phosphorylation potential, through the NaK ATPase, therefore, inherently effects a change in the steady state level of ions inside and ions outside of a cell with the net result being a change in the cellular water content in response to a change in the level of osmotically active substances on either side of the cell membrane.

The transmembrane cellular potential is herein viewed as a Donnan potential (see Donnan, F. G. *Chem. Rev.* 1: 73-90, 1924) resulting from the total amount of the non-diffusible osmotically active substances on either side of the cell membrane, and so is not a function of the so-called electrogenic sodium potassium ATPase, as is commonly held. (See *The Cell* (1983) Alberts, B., Bray, D., Lewis, J., Raff, M., Roberts, K., and Watson, J. S., pp 294 Garland, N.Y. Rather the Na/K ATPase (E.C. 3.6.1.3) is viewed as an electro-neutral "osmopump" exporting a net of 1 $Na^-$ and 1 $Cl^-$ from intracellular to extracellular space for each ATP hydrolyzed. The reaction of the NaK ATPase is treated as the near-equilibrium link between intra- and extracellular electrolytes in the manner given in equation 7.

Cellular water volume can be measured by known (e.g. conventional) techniques involving the distribution of inulin and tritiated water.

Distribution of major inorganic electrolytes between intracellular and extracellular fluid can be measured by known (e.g. conventional) techniques, such as flame photometry, atomic absorption spectoscopy, van Slyke gas analysis, and the like.

Transmembrane cellular potential can be measured by known (e.g. conventional) techniques; such as with electrodes or microprobes, and the like. Calculation of such cellular voltage can be achieved from a measurement of the distribution of chloride ions between intracellular and extracellular fluid following Nernst's law.

A quantitative relationship is theorized to exist involving redox state, phosphorylation potential and the above referenced three states. This relationship may be expressed by the following equation. (7.)

$$\Delta G = O = \Delta G^0_{ATPase} + \Delta G^0_{[Na\ out]/[Na\ in]} \cdots + $$
$$RT \ln [\Sigma ADP][\Sigma Pi]/[\Sigma ATP] + RT \ln \{[Na^+]_o^3/[Na^+]_i^3 \times $$
$$[K^+]_i^2/[K^+]_o^2 \times [Cl^-]_o/[Cl^-]_i\} + T\Delta S$$

wherein:

The values of the various terms in the foregoing equation of are given for muscle or brain as follows: (7.1)

$$\Delta G = O = -7.73\ kcal/mol + O + (-6.3\ kcal/mol) + $$
$$8.4\ kcal/mol + 5.6\ kcal/mol$$

In the foregoing equation, the phosphorylation potential is shown to be in a state of near-equilibrium with the substrates of the sodium potassium ATPase. Since the chloride ion is cell wall permeable, this ion distributes itself in conformity with the transmembrane cellular potential. Movement of three sodium ions out of the cell and two potassium ions into the cell across the cell membrane necessarily results, from the law of electrical neutrality, in the movement of one chloride ion from inside the cell to outside the cell across the cell membrane. This makes the the sodium potassium ATPase, in effect, an osmopump resulting in the export of two milliosmoles per ATP hydrolysed. This pump is electroneutral.

The T delta S term, which is approximately 5.6 kilocalories per mole of ATP hydrolysed, is an entropy term. It, therefore, refers to the state of randomness within the cell. The positive nature of this entropy term indicates that a high degree of order is imposed on the intracellular environment. In terms of quantum and statistical mechanics, the number of ways of achieving a certain energy state is called its degeneracy ($\Omega$). The Boltzman equation defines S (or entropy) as $S = K_b \ln \Omega$, where Boltzmann's constant (which relates the gas constant to Avogadro's number), or $K_B = 1.38 \times 10^{-23}$ J./°K.

It follows from the foregoing equation 7, above, that the distribution of calcium inside the cell is a function of the cube of the respective sodium concentrations inside and outside of the cell because of the action of the high-activity sodium-calcium exchange enzyme. The following equation shows the relationship:

$$K_{Na/Ca} = \frac{[Na^+]_i^3}{[Na^+]_o^3} \cdot \frac{[Ca^{2+}]_o}{[Ca^{2+}]_i} \cdot \frac{[Cl^-]_i}{[Cl^-]_o}$$

where: $[\ ]_i$ intracellular concentration in cytoplasmic $H_2O$ and $[\ ]_o$ concentration in extracellular $H_2O$.

Unlike the simple NaK ATPase which moves 2 mOsmoles out of the cell thus moving $H_2O$ with it, the result of moving $Ca^{2+}$ out of the cell by the Na-Ca exchanger is to move a net of 3 mosmoles into the cell, thus increasing the cell's water content. The NaK ATPase must then operate again to move the excess sodium out in exchange for $K^+$ to restore osmoic equilibrium between extracellular space $H_2O$ and cell $H_2O$.

The net result of the foregoing equation (7) is that the water of both intracellular and extracellular fluid is a function of the sodium/potassium ATPase (E.C. 3.6.1.3) and also of the phosphorylation potential.

It can be empirically seen that the voltage across a cell membrane is inversely related to the chloride distribution and the phosphorylation potential.

Correlation between phosphorylation potential, intracellular chloride and transmembrane cellular potential for various mammalian tissues is illustrated by Table II below:

Correlation between Phosphorylation Potential, Intracellular
Chloride and Transmembrane Cellular Potential.

|  | $\frac{[\Sigma ATP]}{[\Sigma ADP][\Sigma Pi]}$ $M^{-1}$ | $[Cl^-]$ mEq/l | $\Delta E$ mV |
|---|---|---|---|
| red cell | 7,000 | 90 | −9 |
| liver | 15,000 | 40 | −40 |
| brain or muscle | 30,000 | 7–9 | −70 |

From the table above, it is seen that low phosphorylation potential correlates with a high intracellular chloride, and a low transmembrane cellular potential correlates with the inherent setting of the potential as a function of the Donnan-active material within the cell with the phosphorylation potential merely overcoming the Donnan forces so as to export two milliosmoles, as described in equation 7.

It follows, therefore, that the induction of high extra cellular chloride, such as occurs, for example, in current perfusion fluids, must have profound pathological consequences for the metabolism of the cell, even though the purpose of such is to preserve the natural characteristics of the tissue in vitro is to normalize the water and electrolyte concentrations of the various tissue cellular compartments. This is so because the ratio: $\{[Na^+]_o^3 \cdot [K^+]_o^2 \cdot [Cl^-\ ]/\}/[Na^+]_i^3 \cdot [K^+]_o^2 \cdot [Cl^-]_i$ and the T$\Delta$S term link the cellular phosphorylation and the cellular redox states to intracellular and extracellular water and the electrolyte concentrations of $Na^+$, $K^+$, $Cl^-$, and also $Ca^{2+}$.

E. Electrolyte Solution Preparation

The electrolyte solutions of the present invention can be prepared by any convenient or conventional procedure.

As a matter of accuracy, the compositions of this invention can be described in terms of their ion contents which can be expressed either in terms of millimoles per liter of solution, or milliequivalents per liter of solution. It is standard practice in this art in describing a given solution to separate anions from cations, and nonionics from ionic materials; this practice is followed herein in the main. As those skilled in the art will readily appreciate, a translation or conversion of millimoles per liter of solution, or of milliequivalents per liter of solution, into grams of a given salt added per liter of water is routine and is given in any standard text book in the field, such as, for example, *Data For Biochemical Research* (1969) (Dawson, R. M. C., Elliott, W. H., Jones, K. M., EDS) Clarendon Press, Oxford at pages 507 and 508. This reference illustrates not only the salt starting materials, but also the order of addition of same in the preparation of certain illustrative prior art electrolyte solutions shown therein. Solutions of this invention are readily prepared by this type of procedure. The particular salt combination used for a given solution may change from time to time in a manufacturing operation as those skilled in the art well know. The significant factor is that the final concentrations of respective component ions in any given solution remain as specified or desired. In view of the developed state of this art, no detailed description of electrolyte solution preparation procedures is believed to be necessary or desirable herein.

The solutions of this invention, and the component materials incorporated thereinto, are, in general, formulated, so as to achieve the desired physiological Na:Cl milliequivalent ratio normality, and the desired capacity to regulate, correct, and normalize the conditions and states above identified herein. Thus, by this practice of this invention, one can accomplish in a physiologically acceptable manner the removal of metabolic products from cellular water, the replacement of cellular fluids and electrolytes, and the administration of nutrients, and the like, and the growth of cells in culture. The solutions may be administered in any fashion desired so long as they contact living tissue, cells or aggregations of cells. Contacting can be accomplished by any convenient technique, such as, for example, by perfusion of whole organs, across a semi-permeable membrane in cell suspensions, in tissue slices, in cells cultured either on plates, in roller bottles, in suspensions and the like, as those skilled in the art will readily appreciate. The solutions of this invention as prepared are, in general, well suited for the administration of therapeutic agents to cells in any form in vitro.

When bicarbonate anions are not present, then the level of combined (or sigma) l-lactate/pyruvate and/or d-betahydroxybutyrate/acetoacetate present in a solution of this invention is optionally greater than when bicarbonate is present in order to achieve the desired milliequivalent ratio of sodium to chloride, as indicated. The concentration of either sigma l-lactate/pyruvate and/or of d-betahydroxybutyrate/acetoacetate in a given solution of this invention can thus range up to 80 mM. It is present preferred, particularly when no bicarbonate is present, to employ a mixture of l-lactate/pyruvate with a mixture of d-betahydroxybutyrate/acetoacetate.

Those skilled in the art will realize that in any given solution of this invention one can incorporate an excess of one or more individual members of any one mixture couple of this invention so that (a) the ratio of one member to the other of any given couple and (b) the total quantity of both mixtures or members lies outside of the ranges hereinabove described. Such a single member excess is not recommended when practicing the present invention. However, if such a single member excess does occur, the amount of the excess can be calculated by determining the maximum ratio of one couple member to the other which can be present in accord with the above teachings, and then the quantity of one couple member remaining (or present) which is outside of this ratio range may be considered to constitute an excess. The effect of such an excess is evidently merely to cut down, but not to eliminate, the efficacy of what effect would otherwise be obtained by using only a solution which contains mole ratios and quantities of respective mixture couples within the spirit and scope teachings of this invention.

In the making of solutions of this invention, it is preferred to employ the optically active l-lactate state or l-lactic acid (which will make the desired L-lactate anions in solution), and also similarly to employ d-betahydroxybutyric acid or d-betahydroxybutyrate salts (will make the desired d-betahydroxybutyrate anions in solution). Choice of particular salt or acid (or mixture) used in any given case depends among various factors, such as upon the other starting inorganic salts which a formulator desires to use (based upon availability, cost, and like factors), all as will be readily appreciated by those skilled in the art. Racemic (d,l) mixtures could be used, but their use is preferably avoided. If such are used, the ratios of one member to another in the respective near-equilibrium couples involved should be based upon the quantity of particular optically active form present (e.g., either [l-lacetate$^-$] or [d-betahydroxybutyrate$^-$], s the case may be).

The carbon dioxide, when used, can be introduced either as a gas, preferably using conventional aeration apparatus to effect a solubilization of $CO_2$ in a solution, or it can be generated in-situ from a dissolved metal (such as sodium, (preferred), potassium, calcium or magnesium) salt of bicarbonate in combination with a dissolved acid (lactic, pyruvic, betahydroxybutyric, or acetoacetic) in respective proportions of each such that the total quantity of dissolved carbon dioxide so generated is within the ranges described herein for use in a solution of this invention.

As elsewhere indicated herein, if desired, a solution of this invention can also contain various known nutrient additives in an amount ranging, for example, from about 1 to 50 millimoles per liter such as, for example, Basal Eagle's Media for use in tissue culture. For a listing of the small and varied components usually added to the "Balanced Salt Solution" of tissue culture media described here (see Eagele, H. *Science* 122 501,1955; Eagle, H. et al. *Science* 123,845, 1956; Eagle, H. *J. Biol. Chem.* 214, 839, 1955; and many other similar lists of additives currently sold commercially as tissue culture media).

In general, a solution of this invention should contain as a minimum of total of sigma (lactate/pyruvate and/or sigma betahydroxybutyrate/acetoacetate) and/or sigma bicarbonate/carbon dioxide which is at least about 0.1 millimoles per liter as indicated. Below these levels, benefits in normalization of body metabolism as explained above are apparently achievable, but such benefits become increasingly difficult to demonstrate and prove by state of the art techniques of measurement. Consequently, it is preferred to avoid, if possible, homeopathic possibilities by using minimum concentrations as above indicated.

When bicarbonate is present, the total quantity of sigma (lactate/pyruvate and/or betahydroxybutyrate/acetoacetate) used can generally be reduced which is now believed to be desirable. Thus, when bicarbonate is present, the total sigma (l-lactate/pyruvate and/or d-betahydroxybutyrate/acetoacetate) is preferably about 2 to 17 millimoles per liter.

When a solution of this invention contains at least one metabolizable nonionic or zwitterionic osmotically active substance, added to provide nutritional requirements no account of the proper Na:Cl ratio need be considered as for instance after addition of glucose and glutamine. When for examples, compounds like Na glutamate or lysine Cl is added in a nutritive mixture, amounts over 1 meq/l can be compensated for by adjusting the Na and Cl within the basic balanced salt mixture.

F. Compositions & Processes

In summary, the present invention relates to an in vitro process of the type where living animal cells are contacted with an extracellular fluid which contains physiologically effective amounts of inorganic electrolytes. The improvement comprises (a) eliminating hyperchloremia from such cells so contacted by maintaining in said extracellular fluid a sodium to chloride milliequivalent ration in the range from about 1.24 to 1.60, and (b) simultaneously maintaining in said cells:

(1) a normal redox state,
(2) a normal phosphorylation potential, and
(3) a normal intracellular fluid pH by including in said extracellular fluid each of the following dissolved components in the respective amounts indicated:

(A) at least one of the following near-equilibrium couples in the respective quantities indicated:
(1) from 0 to about 55 millimoles per liter of a first couple mixture consisting of bicarbonate anions and carbon dioxide wherein the milliequivalent ratio of said bicarbonate anions to said carbon dioxide ranges from about 8/1 to 50/1.
(2) from 0 to abot 55 millimoles per liter of a second couple mixture consisting of l-lactate anions and pyruvate anions wherein the milliequivalent ratio of said l-lactate anions to said pyruvate anions ranges from about 20:1 to 1:1,
(3) from about 0 to about 55 millimoles per liter of a third couple mixture consisting of d-betahydroxybutyrate anions and acetoacetate anions wherein the milliequivalent ratio of said d-betahydroxybutyrate to said acetoacetate ranges from about 6:1 to 0.5:1.
(A) from about 130 to 170 millimoles per liter of sodium cataions,
(B) sufficient millimoles per liter of chloride anions to produce a milliequivalent ratio of sodium cations to chloride anions in the range from about 1.24 to 1.6,
(C) optionally from 0 to about 6000 millimoles per liter of at least one osmotically active substantially nonionic substance,
(D) from 0 to about 18 millimoles per liter, of total inorganic phosphate,
(E) optionally at least one of the following additional cations in a respective quantity as indicated:

| cation | quantity (in millimoles/liter) |
|---|---|
| potassium | 1-6 |
| calcium | 0-3 |
| magnesium | 0-1.3 | the relationship between said water and all solutes in said water being such that said solution is characterized by having:

(1) an osmolarity ranging from 260 to 6400 milliosmoles;
(2) a pH in the range from about 6.9 to 7.8,
(3) the charges of all cations equal the charges of all anions; and
(4) the minimum total concentration of all said near-equilibrium (couple(s) present in said solution is at least about 0.1 millimoles per liter.

In summary compositions of this invention can be described by the following Table IV:

TABLE IV

| Component | Quantity Range (millimoles per liter) |
|---|---|
| Total cations (mEg/L) | about 130 to 170 |
| (1) sodium+ | about 130 to 170 |
| (2) potassium+ | about 0 to 6 |
| (3) calcium++ | about 0 to 3 |
| (4) magnesium++ | about 0 to 1.3 |
| Total anions (mEg/L) | about 130 to 170 |
| (5) chloride− | about 81 to 137 |
| (6) bicarbonte− | about 0 to 55 |
| (7) l-lactate− plus pyruvate− | about 0 to 55 |
| (8) d-betahydroxybutyrate− + acetoacetate− | about 0 to 55 |
| (9) $Pi^{-1.8}$ | about 0 to 18 |
| (10) sum (6 + 7 + 8) | about 26 to 80 |
| Total nonionics | about 0 to 6000 |
| (1) carbon dioxide | about 0 to 8.7 |
| (2) others | about 0 to 6000 | the relationship between said water and said components being such that:

(12) the milliequivalent ratio of $HCO_3^-/CO_2$ ranges from about 8.7/1 to 50/1,
(13) the milliequivalent ratio of l-lactate−/pyruvate− ranges from about 20/1 to 1/1
(14) the milliequivalent ratio of d-betahydroxybutyrate−/acetoacetate− ranges from about 6/1 to 0.5/1
(15) the millieqivalent ratio of Na:Cl ranges from about 1.24-1.6 and preferably 1.30-1.45
(16) the osmolarity millimoles per liter ranges from about 260-6400, and
(17) the solution pH ranges from about 6.9 to 7.8

In practice, the compositional limits of electrolytes used in (a) balanced salt solutions for tissue culture, (b) perfusion media for perfusions of organs, or (c) incubation media for tissue slices, minces, homogenates, or isolated cells and the like, are much smaller that the corresponding limits used in in vivo solutions for electrolytes and fluid therapy where disordered conditions either prexist or are purposely being made (see, for example, the in vivo solutions described in my copending case identified by U.S. Ser. No. 623,102 filed June 22, 1984, now abandoned, but refiled as U.S.Ser. No. 748,232 filed June 24, 1985 and U.S. Ser. No. 623,510).

Also in practice, perfusion media may contain bovine serum albumin as known in the art (see Table II above). If a polyanion ia used, no compensation is needed (for example, when carboxymethyl starch is substituted for albuminate. In tissue culture it is not customary to add polyvalent anions in concentrations which require use of increased cation levels (since fetal calf serum is added typically as a 10% solution). Thus, in the main, the solutions of this invention are intended to provide an improved electrolytes composition with a normal Na:Cl ratio, a physiologic pH, and a regulation of redox state and phosphorylation state if desired. To such a solution one may add any combination of nutrients, macromolecules, or the like so long as the sodium and chloride on such additives are compensated for so as to maintain such concentrations at those herein described.

Osmotically active substances (including zwitterions) may be used as desired. It is clear that, basically, as Table III shows, the existing balanced salt mixtures are either Krebs-Henseleit with altered Ca & Mg (see Ex. 10, 2, 23, 24, and 25 of Table III) or Krebs Ringers phosphate (see Ex. 26 and 11 of Table III). It is further clear from Table V that example 27-30 differs radically from prior art balanced salt solutions. They also differe from all prior art perfusion media (see Table II, Ex. 15-19) which have an abnormal Na:Cl ratio with the exception of solution 20, Table II which normalized the Na:Cl with acetate with the now known toxic consequences since acetate does not constitute a safe entry point.

The way that the albumin was used in the prior art did not correct the abnormal Na:Cl ratio in the prior art solutions. In the prior art, albumin was used to ge improved flow through capillaries improved viscosity during perfusion and reduced sticking together of cells during incubation. These prior art benefits may be utilized in the present invention if albuminate is added to a balanced salt solution of the present invention. New results are obtained, not known to or achieved in, the prior art because, for o±e thing, the present solutions offer the ability to maintain a normal Na:Cl ratio and a normal anion gap.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLES 27-30

The compositions here described in Table V are balanced salt solutions of the present invention prepared as taught by Dawson et al., reference cited.

For comparison purposes, Table VI is provided with Examples 31-34 to illustrate the compositional differences which exist for compositions which contain polyanions.

TABLE V

New Normochloremic Salt Mixtures for Use in the Absence of Polyanions

| Units mmoles L fluid | Normal Plasma N.E.J.M. 283, 1285 1970 | 27 Redox-Balanced Normo-chloremic | 28 Redox-Balanced Normo-chloremic | 29 Veech's Salt's | 30 Veech's Minimal Salts | 30a Veech's Minimal Salts with Decreased Water |
|---|---|---|---|---|---|---|
| Na | 136–145 | 138 | 139 | 142 | 142 | 142 |
| K | 3.5–5.0 | 4.5 | 4.5 | 4.5 | 4.5 | 4.5 |
| Ca | 2.1–2.6 | 1.5 | 1.1 | 1.1 | 1.1 | 1.1 |
| free [$Ca^{2+}$] | [1.06] | | | [1.06] | [1.06] | |
| Mg | 0.75–1.25 | 0.7 | 0.6 | 0.56 | 0.56 | 0.56 |
| free [$Mg^{2+}$] | [0.53] | | | [0.53] | [0.53] | |
| $\Sigma$ mEq Cations | 142.7–153.2 | 146.7 | 146.9 | 149.73 | 149.82 | 149.82 |
| Cl | 100–106 | 102 | 102 | 102 | 102 | 102 |
| $HCO_3$ | 26–28 | 29 | 29 | 29 | 45.79 | 29 |
| $\Sigma$ Pi | 1–1.45 | 1.2 | 1.2 | 1.1 | 1.1 | 1.1 |
| $SO_4$ | 0.32–0.94 | 0.1 | 0 | 0 | 0 | 0 |
| L-lactate | 0.6–1.8 | 11.6 | 8.85 | 10.27 | — | 10.2 |
| pyruvate | | 1.7 | 0.89 | 1.47 | — | 1.47 |
| Lact/pyr | | 7 | 10 | 7 | | 7 |
| D-$\beta$-OHbutyrate | | | 3 | 3 | — | 3 |
| acetoacetate | | | 1 | 2 | — | 2 |
| $\beta$-HB/acac | | | 3 | 1.5 | — | 1.5 |
| acetate | | | | | | |
| Other | | | | | | |
| $\Sigma$ mEq anions | 128.7–139.4 | 146.7 | 146.5 | 149.72 | 149.72 | 149.72 |
| NaCl | 1.28–1.45 | 1.35 | 1.36 | 1.39 | 1.39 | 1.39 |
| Glucose or others | 3.9–5.6 | 0 | 0 | 10 | 10 | 10 4–6 M urea |
| $CO_2$ | 0.99–1.39 | 1.54 | 1.54 | 1.54 | 2.29 | 1.54 |
| pH | 7.35–7.45 | 7.4 | 7.4 | 7.4 | 7.4 | $\approx$7.4 |
| $\Sigma$ mOsm | 285–295 | 292 | 293 | 307 | 307 | 4– to 6,300 |
| Use: | | Tissue culture, physiologic experiments, organ perfusion. | Alternative to 27 | Alternative to 28 | Alternative to 27 without redox control | For cryopreservation of tissues with glycerol kinase |

TABLE VI

Normochloremic Salt Mixtures for Use with Polyanions.

| Units mmoles L fluid | Normal Plasma N.E.J.M. 283, 1285 1970 | 31 Krebs Albuminate | 32 Krebs Albuminate + L/P | 33 Krebs Albuminate + L/P + $\beta$-HB/AcAc | 34 Veech's Polyanionate |
|---|---|---|---|---|---|
| Na | 136–145 | 138 | 143 | 145 | 142 |
| K | 3.5–5.0 | 4.0 | 4.0 | 4.0 | 4.5 |
| Ca | 2.1–2.6 | 2.25 | 2.25 | 2.25 | 1.1 |
| free [$Ca^{2+}$] | [1.06] | | | | |
| Mg | 0.75–1.25 | 1.0 | 1.0 | 1.0 | 0.56 |
| free [$Mg^{2+}$] | [0.53] | | | | |
| $\Sigma$ mEq Cations | 142.7–153.2 | 148.5 | 153.5 | 155.5 | 149.73 |
| Cl | 100–106 | 103 | 103 | 103 | 102 |
| $HCO_3$ | 26–28 | 29 | 29 | 29 | 29 |
| $\Sigma$ Pi | 1–1.45 | 1.2 | 1.2 | 1.2 | 1.1 |
| $SO_4$ | 0.32–0.94 | — | — | — | — |
| L-lactate | 0.6–1.8 | | 4.375 | 4.375 | |
| pyruvate | | | 0.625 | 0.625 | |
| Lact/pyr | | | 7 | 7 | |
| D-$\beta$-OHbutyrate | | | | 1.2 | |
| acetoacetate | | | | 0.8 | |
| $\beta$-HB/acac | | | | 1.5 | |
| acetate | | | | | |
| Other (Polyanionate) | | 0.73 Alb (−14.6 mEq) | 0.73 Alb (−14.6 mEq) | 0.73 Alb (−14.6 mEq) | Carboxy-methyl starch (−16.73 mEq) |
| $\Sigma$ mEq anions | 128.7–139.4 | 148.8 | 153.8 | 155.8 | 149.73 |
| NaCl | 1.28–1.45 | 1.34 | 1.39 | 1.40 | 1.39 |
| Glucose or others | 3.9–5.6 | — | — | — | — |
| $CO_2$ | 0.99–1.39 | 1.54 | 1.54 | 1.54 | 1.54 |
| pH | 7.35–7.45 | 7.4 | 7.4 | 7.4 | 7.4 |
| $\Sigma$ mOsm | 285–295 | 280.7 | 290.7 | 294.7 | 307 |
| Use: | | 5 g % of Na Albuminate multiple uses | with control of cytoplasmic redox state | with control of cytoplasmic & mitochondrial redox state | Alternative to albumin |

EXAMPLE 35

Fibroblasts are grown in tissue culture balanced salt solutions of two types to which is added Eagles Basal Media to both salt mixtures.

TABLE VII

Eagle's Nutrients Additives to Balanced Salt Mixtures

| COMPONENT | BME (modified) (1X) Liquid without Glutamine mg/L |
|---|---|
| Dextrose | 1000.0 |
| Phenol Red.Na | 17.0 |
| Sodium Succinate 6H$_2$O | |
| AMINO ACIDS | |
| L-arginine HCl | 21.06 |
| L-cystine | 12.01 |
| L-cystine, Na$_2$ | |
| L-glutamine | |
| L-histidine HCl H$_2$O | 10.50 |
| L-isoleucine | 26.23 |
| L-leucine | 26.23 |
| L-lysine HCl | 36.53 |
| L-methionine | 7.46 |
| L-phenylalanine | 16.51 |
| L-threonine | 23.82 |
| L-trytophan | 4.08 |
| L-tyrosine | 18.11 |
| L-valine | 23.43 |
| VITAMINS | |
| Biotin | 1.00 |
| D-CaPantothenate | 1.00 |
| Choline Bitratrate | |
| Choline Chloride | 1.00 |
| Folic Acid | 1.00 |
| I-inositol | 2.00 |
| Nicotinamide | 1.00 |
| Pyridoxal HCl | 1.00 |
| Riboflavin | 0.10 |
| Thiamin HCl | 1.00 |

References:
1. Eagle, H., 1955, Science 122:501
2. Eagle, H., 1955, J. Exp. Med., 102:37
3. Eagle, H., 1955, J. Exp. Med., 102:595
4. Eagle, H., 1955, J. Biol. Chem., 214:839
5. Eagle, H. et al., 1956, Science, 123:845
6. Eagle, H., 1955, Proc. Soc. Exp. Biol. Med., 89:362
7. Morton, H. J., 1970 in Vitro, 6:89
8. Hanks, J. H., Wallace, R. E., 1949, Proc. Soc. Exp. Biol. Med., 71:198

The composition of the Balanced Salt Mixtures used are taken from Table III and Table V.

TABLE VIII

Composition of 2 Balanced Salt Mixtures for Tissue Culture.

| mmoles/L | Earle's Balanced Salt Example 22- Table III | Veech's Salts Example 29- Table V |
|---|---|---|
| Na | 142 | 142 |
| K$^+$ | 5.4 | 4.5 |
| Ca$^{2+}$ | 1.8 | 1.1 |
| Mg$^{2+}$ | 0.8 | 0.56 |
| meq Cations | 152.6 | 149.73 |
| Cl$^-$ | 126.2 | 102 |
| HCO$_3^-$ | 23.8 | 29 |
| Pi$-1.8$ | 1.0 | 1.1 |
| SO$_4^{2-}$ | 0.8 | 0 |
| L-lactate$^-$ | 0 | 10.27 |
| pyruvate | 0 | 1.47 |
| Lact/pyr | — | 7 |
| D-B-Hydroxybutyrate | | 3 |
| acetoacetate | 0 | 2 |
| HB/acac | — | 1.5 |
| meq anions | 153.4 | 149.72 |
| Na:Cl | 1.12 | 1.39 |
| CO$_2$ | 1.23 | 1.54 |
| pH | 7.4 | 7.4 |
| mOsm | 311 | 307 |

Methods:
Cells are grown in roller bottles in the conventional manner, one in 5% CO$_2$ the other in 6% CO$_2$ with media changed every two days.

Results:
Growth rate

It is noted that the fibroblasts reach confluence in 7 days using salts from example 29, but take 10 days to reach confluence using salts from example 22. It is concluded that the new salt mixture facilitates growth of cultured cells.

Phosphorylation Potential:

On day six of the culturing procedure, 1 hour after the media was changed, the cells were killed by addition of perchloric acid and then metabolite contents were measured as described in Veech et al. *J Biol Chem* 254: 6538–6547, 1979, to evaluate their redox and phosphorylation states.

TABLE IX

| | Earle's Salts example 22 | Veech's Salts example 29 |
|---|---|---|
| cytoplasmic | 1,000 | 1,000 |
| $\dfrac{[NAD^\pm]}{[NADH]}$ | | |
| cytoplasmic | 12,000 | 10,000* |
| $\dfrac{[\Sigma\ ATP]}{[\Sigma\ ADP][\Sigma\ Pi]^{M-1}}$ | | |

It is noted that the phosphorylation potential is significantly elevated in the cells grown in Earl's salts and normal for fibroblasts grown in the salt solution of the present invention.

Morphology:

Another set of cells is exposed to glutaraldehyde and fixed for electron microscopy. It is noted that fibroblasts grown in Earle's salts have disordered or abnormal intracellular structure whereas those grown in the salt solution of the present invention appear like normal fibroblasts.

It is noted that the phospho ylation state of cells incubated in Krebs Henseleit is abnormally elevated whereas that of cells incubated in so-called Krebs Albuminate solution of the present invention with a normal Na:Cl ratio have a normal phosphorylation state.

EXAMPLE 36

Hepatocytes are made and incubated as described by Crow, K. E., Cornell, N. W. & Veech, R. L. *Alcoholism, Clin. & Exp. Res.* 1. 43–47, 1977.

One set is incubatd in Krebs-Henseleit solution to which is added 5 mM of a sum of Na lactate and Na pyruvate in a 7:1 ratio (example 10, Table III) and another set of cells is incubated with lactate/pyruvate as described in Krebs Albuminate solution of the present invention (example 32 Table VI).

After 1 hour incubation the cells are centrifuged into perchloric acid under bromododecane and their metabolite contents measured.

Results:

TABLE X

| Nucleotide Ratios | | |
|---|---|---|
| | Krebs Henseleit | Krebs Albuminate |
| cytoplasmic | 1,500 | 1,500 |

-continued

| Nucleotide Ratios | | |
|---|---|---|
| | Krebs Henseleit | Krebs Albuminate |
| $\dfrac{[NAD]}{[NADH]}$ | | |
| $\dfrac{[\Sigma\ ATP]}{[\Sigma\ ADP][\Sigma\ Pi]^{M-1}}$ | 20,000* | 15,000 |

We note that the phosphorylation potential in cells incubated in Krebs-Henseleit with a Na:Cl rates of 1:12 is greater than the phosphorylation potential in hepatocytes incubated in Krebs-Albuminte where the Na:Cl ratio is 1:34.

This shows that there the NaCl ratio in the external media surrounding cells an influence the central internal energy status of the cell. It further shows that the system behaves like a near-equilibrium one.

The teachings contained in my co-pending applications identified by U.S. Ser. Nos. 623,101; 623,102; 623,443; and 623,510 all filed June 22, 1984 and now abandoned, but refiled as, respectively, U.S. Ser. No. 747,858; 748,232; 748,184; and 747,792 all filed June 24, 1985.

It will be appreciated that many variations and further embodiments of the present invention will be apparent to those skilled in the art from the foregoing teachings and no unnecessary limitations are to be drawn therefrom.

I claim:

1. An in vitro process suitable for at least one of tissue culture, organ perfusion, cell incubation, and organ preservation comprising contacting living animal cells with a basic electrolyte solution to which nutrients can be added, said solution comprising:
   (a) from 136 to 155 millimoles per liter sodium,
   (b) sufficient chloride to produce a sodium to chloride milliequivalent ratio of from 1.28 to 1.45, and
   (c) from 0.5 to 10 millimoles per liter of at least one of the following:
      (1) l-lactate and pyruvate, the l-lactate to pyruvate milliequivalent ratio being 3:1 to 15:1, and
      (2) d-betahydroxybutyrate and acetoacetate, the d-betahydroxybutyrate to acetoacetate milliequivalent ratio being 4:1 to 1:1.

2. The process of claim 1 wherein said solution additionally comprises at least two metal cations selected from the group consisting of 1 to 5 millimoles per liter potassium, 0.2 to 1.5 millimoles per liter calcium, and 0.2 to 1 millimoles per liter magnesium.

3. The process of claim 1 wherein said solution additionally comprises fom 10 to 55 millimoles per liter of bicarbonate and dissolved carbon dioxide, the bicarbonate to $CO_2$ ratio being about 10:1 to 32:1.

4. The process of claim 1 wherein said solution additionally comprises sufficient osmotically active dissolved nutrient materials selected from the group consisting of nonionics and zwitterionics to produce a solution osmolarity ranging from 265 to 550 milliosmoles per liter.

5. The process of claim 1 wherein said contacting comprises perfusing an organ from a mammal for a time and under condions sufficient to maintain said organ.

6. The process of claim 1 wherein said living animal cells comprise tissue being cultured and said solution additionally comprises from 1 to 50 millimoles per liter of nutrients.

7. The process of claim 1 wherein said solution additionally comprises from 0 to 18 millimoles per liter of total dissolved inorganic phosphate.

8. The process of claim 1 wherein said solution additionally comprises from 0.05 to 4 millimoles per liter polyanionate.

9. The process of claim 8 wherein said polyanionate is albuminate.

10. A fluid medium for living animal cells comprising on the basis of one liter of solution:
    (a) from 136 to 155 millimoles per liter sodium,
    (b) sufficient chloride to produce a sodium to chloride milliequivalent ratio of from 1.28 to 1.45, and
    (c) from 0.5 to 10 millimoles per liter of at least one of the following:
       (1) l-lactate andpyruvate, the l-lactate to pyruvate milliequivalent ratio being 3:1 to 15:1, and
       (2) d-betahyroxybutyrate and acetoacetate, the d betahydroxybutyrate to acetoacetate milliequivalent ratio being 4:1 to 1:1, and
    (d) from 1 to 50 millimoles per liter of nutrients, said solution having a pH ranging from 6.9 to 7.8, and an osmolarity ranging from 265 to 550 milliosmoles per liter.

11. The medium of claim 10 which additionally contains from 10 to 55 millimoles per liter of bicarbonate and dissolved carbon dioxide, the bicarbonate to $CO_2$ concentration ratio being 10:1 to 32:1.

12. The medium of claim 10 which additionally contains at least two metal cations selected from the group consisting of: 1 to 5 millimoles per liter potassium, 0.2 to 1.5 millimoles per liter calcium, and 0.2 to 1 millimoles per liter magnesium.

13. The fluid medium of claim 10 containing sufficient dissolved osmotically active materials to produce in said medium an osmolarity ranging from 300 to 6000 milliosmoles per liter, said osmotically active materials being selected from the group consisting of urea and glycerol, said medium being suitable for cryopreservation of organs.

14. The medium of claim 10 which contains about 0.5 to 55 milliequivalents per liter of polyanionate.

* * * * *